United States Patent [19]

Yen et al.

[11] Patent Number: 5,599,919
[45] Date of Patent: Feb. 4, 1997

[54] NUCLEIC ACID ENCODING A TRANSIENTLY-EXPRESSED KINETOCHORE PROTEIN, AND METHODS OF USE

[75] Inventors: Timothy J. Yen, Havertown, Pa.; Jerome B. Rattner, Calgary, Canada

[73] Assignees: Fox Chase Cancer Center, Philadelphia, Pa.; UTI, Inc., Calgary, Canada

[21] Appl. No.: 353,700

[22] Filed: Dec. 9, 1994

[51] Int. Cl.$^6$ ............................ C12N 15/12; C12N 15/00
[52] U.S. Cl. ............................ 536/23.5; 435/172.3; 935/9
[58] Field of Search ........................ 536/23.5; 435/172.3

[56] References Cited

FOREIGN PATENT DOCUMENTS 9412521  6/1994  WIPO .

OTHER PUBLICATIONS

Zhu et al. (1995) Mol. Cell. Biol. 15: 5017–5029.
Dalmau et al., 1990, Ann. Neurol., 27:544–552.
Gerdes et al., 1983, Int. J. Cancer, 31:13–20.
Hall et al., 1990, J. Pathol., 162:285–294.
Hitchock, C. L., 1991, Am. J. Clin. Pathol., 96:444–445.
Kreipe et al., 1993, Am. J. Pathol., 142:651–657.
Leonardi et al., 1992, J. Clin. Pathol., (London) 45:416–419.
Mathews et al., 1984, Nature, 309:374–376.
Miyachi et al., 1978, J. Immunol., 121:2228–2234.
Peterson, C. L., 1994, Cell, 79:389–392.
Peterson et al., 1992, Neurology, 42:1931–1937.
Rattner et al., 1993, Cell Motility and the Cytoskeleton, 26:214–226.
Rattner et al., 1991, J. Immunol., 146:2341–2344.
Rattner, J. B., Principles of Clinical Flow Cytometry; in *Clinical Flow Cytometry Principles and Applications*, Bauer, Duque and Sharkey eds. (1993), pp. 28–40.
Sampson et al., 1992, J. Pathol. 168:179–185.

*Primary Examiner*—Robert A. Wax
*Assistant Examiner*—Ge Bugaisky
*Attorney, Agent, or Firm*—Janet E. Reed; Dann, Dorfman, Herrell & Skillman

[57]  ABSTRACT

An isolated nucleic acid is provided which encodes a transiently-expressed kinetochore protein, CENP-F. Also provided are the purified polypeptide encoded by the nucleic acid sequence, and antibodies immunologically specific for the polypeptide. These biological molecules are useful as markers of cellular proliferation, particularly for the identification of cells in the G2 and M phases of the cell cycle. Methods are provided for using the nucleic acid, protein and antibodies for assessing cellular proliferation in biological fluids and tissue samples, and for detecting the presence of autoantibodies to the protein.

6 Claims, 1 Drawing Sheet

NUCLEIC ACID ENCODING A TRANSIENTLY-EXPRESSED KINETOCHORE PROTEIN, AND METHODS OF USE

Pursuant to 35 U.S.C. §202(c), it is hereby acknowledged that the U.S. Government has certain rights in the invention described herein, which was made in part with funds from the National Institutes of Health.

FIELD OF THE INVENTION

This invention relates to detection of cellular proliferation for diagnosis and prognosis of neoplastic disease. More particularly, this invention provides a novel nucleic acid molecule, protein and antibodies useful for detecting cellular proliferation.

BACKGROUND OF THE INVENTION

The centromere is a multi-functional chromosomal domain that plays a major role in cell proliferation by mediating both chromosome movement and sister chromatid association during cell division. The kinetochore is a highly complex macromolecular structure associated with centromeric heterochromatin. The kinetochore is responsible for establishing and maintaining connections with microtubules of the mitotic spindle.

The identification and molecular cloning of many proteins of the centromere-kinetochore complex, using autoimmune sera and biochemical fractionation, has provided the necessary reagents to investigate the biochemical structure and function of the complex. The collection of proteins thus identified can be separated into two classes, based on their distribution during various times of the cell cycle. One class, the DNA- or chromatin-binding proteins, CENP-A, B, and C, are constitutive centromere proteins, inasmuch as they can be detected throughout interphase, at discrete loci within the nucleus (presumably centromere chromatin), or localized within the centromere-kinetochore complex during mitosis. The other class, comprising well-characterized proteins such as INCENP and CENP-E belong to the facultative family of centromere-kinetochore proteins, because of the transient nature of their association with the kinetochore complex. In the case of the kinesin-like CENP-E protein, it accumulates to high levels in the cytoplasm of interphase cells and assembles onto kinetochores of prometaphase chromosomes after nuclear envelope breakdown.

Measures of cell proliferation, including direct counts of mitotic figures, thymidine labelling, bromodeoxyuridine incorporation, determination of nucleolar morphology and flow cytometry, have been found to be prognostic indicators for a variety of tumor types. In addition, several proliferation-associated nuclear antigens have been identified which have allowed the direct detection and quantitiation of cycling cells by indirect immunofluorescence. One of these, Proliferating Cell Nuclear Antigen (PCNA), is a 36 kDa protein first identified by autoantibodies associated with autoimmune disease (Miyachi et al., J. Immunol. 121: 2228–2234, 1978). This protein is an auxiliary protein of DNA polymerase delta, a nuclear protein that is present throughout the cell cycle but is maximally expressed in the Gl-S phase (Matthews et al., Nature 303: 374–376, 1984). Several reports indicate that PCNA expression is deregulated in tumor cells, making the use of this antigen as a marker of tumor cell proliferation problematic (Hall et al., J. Pathol. 161: 285–294, 1990). A second cell cycle related antigen recognized by the monoclonal antibody Ki-67 has also been used to identify proliferating cells (Gerdes et al., Int. J. Cancer 31: 13–20, 1983). Like Ki-67, K1–K1 is detected from the G1 boundary of the cell cycle through M-phase. However, in contrast to Ki-67, Ki–S1 can be detected in paraffin embedded tissues. One major limitation of all three proliferating cell antigens described above is that they are detected throughout a major portion of the cell cycle, making them of limited use when specific cell cycle information is desired.

We recently identified a novel .ca 400 kDa cell cycle-dependent kinetochore associated protein in human cells, designated CENP-F, using human autoimmune serum (Rattner et al., Cell Motility and the Cytoskeleton 26: 214–226, 1993). Immunofluorescence staining of CENP-F revealed that it was homogeneously distributed throughout the nucleus of HeLa cells in the G2 stage of the cell cycle, and then localized to the centromere region of the chromosomes at prophase after G2. Similar to CENP-E, CENP-F appeared to localize to the outer layer of the kinetochore and was subsequently found at the spindle midzone and within the intercellular bridge during the later part of mitosis. CENP-F was not detected during the G1 phase of the cell cycle, and was presumed discarded or degraded after cytokinesis.

Amongst the small number of facultative centromere-kinetochore proteins that have identified thus far, CENP-F appears to be the earliest member to interact with the centromere-kinetochore complex. For example, the appearance of CENP-F at the centromere-kinetochore region at prophase precedes the appearance of CENP-E. Thus, antibodies immunologically specific for CENP-F could enable the specific detection of G2 and M-phase cells in cultured cells or in tissues, rendering CENP-F a useful addition to the cell cycle specific markers used to study cell proliferation in tumor samples. However, to date, little information is available regarding the molecular characterization of CENP-F; the isolated purified CENP-F protein has heretofore been unavailable, and likewise, nucleic acids encoding the protein have not been produced.

It is an object of the present invention to provide an isolated, purified, nucleic acid molecule that encodes the entire CENP-F polypeptide. It is further an object of the invention to provide an isolated, purified form of the CENP-F protein, and to provide antibodies immunologically cross-reactive with the protein. The nucleic acid, protein and antibodies thereto may be used to advantage in diagnostic and prognostic assays for the detection and measurement of cellular proliferation in cultured cells and in tissues. The use of CENP-F as a cell cycle-specific marker advantageously allows the specific detection of G2 and M-phase cells, which other known cell cycle-specific markers are unable to specifically target. Additionally, the CENP-F protein itself provides the additional benefit of use for detecting autoimmune antibodies to the protein, which may provide an early diagnosis for the onset of various malignant diseases.

SUMMARY OF THE INVENTION

According to one aspect of the present invention, an isolated, purified nucleic acid molecule is provided, which includes a sequence encoding a kinetochore protein, referred herein as CENP-F. The protein is transiently expressed substantially during the G2 and M phases of a cell cycle. To explain the term "substantially during," the protein is detected by immunofluorescence microscopy only during the G2 and M phases of the cell cycle. By Western blot analysis, however, low levels of the protein may be detected at other phases of the cell cycle, but a much high-fold level is detected at the G2 and M phases. The CENP-F protein encoded by the nucleic acid has a molecular weight of between about 340 kDa and 420 kDa, and possesses a general structure comprising two extended coil domains flanking a non-coil core domain.

In a preferred embodiment of the invention, the nucleic acid sequence is of human origin, encoding a polypeptide of approximately 372 kDa in molecular weight and approximately 3248 amino acids in length.

According to another aspect of the present invention, a isolated and purified kinetochore protein, CENP-F, is provided, which is transiently expressed substantially during G2 and M phases of a cell cycle. The protein is preferably of human origin, having the structural characteristics as described above.

According to another aspect of the present invention, antibodies are provided that are immunologically specific for part or all of the isolated protein of the invention. The antibodies may be polyclonal or monoclonal.

According to another aspect of the invention, methods are provided for using the nucleic acid, protein and antibodies of the invention for assessing cellular proliferation in biological fluids and tissues. A method is provided for detecting the presence of autoantibodies to CENP-F in a biological fluid. The method comprises detectably labelling an isolated, purified protein of the invention; preparing a test sample of the biological fluid suspected of containing the autoantibody; contacting the test sample with the detectably labelled protein such that the autoantibody, if present, forms a detectable complex with the labelled protein; and thereafter detecting the complex. Methods are also provided for detecting the presence of CENP-F protein, or nucleic acids encoding the protein, in a biological fluid, cell or tissue. To detect the protein, the method comprises preparing an antibody immunologically specific for the protein; detectably labelling the antibody, preparing a test sample of the biological fluid, cell or tissue suspected of containing the protein; contacting the test sample with the detectably labelled antibody such that the protein, if present, forms a detectable complex with the antibody; and detecting the complex. For detecting a nucleic acid, the method involves preparing a nucleotide probe that specifically hybridizes with the nucleic acid. The nucleotide probe is detectably labelled, a test sample of the biological fluid, cell or tissue suspected of containing the nucleic acid is prepared, and the test sample is contacted with the nucleotide probe such that the nucleic acid, if present, forms a detectable complex with the nucleotide probe. The detectable complex is thereafter detected.

In a preferred embodiment, the foregoing methods may be adapted to measure the quantity of autoantibodies, nucleic acid, or CENP-F protein in a test sample by detectably labelling the appropriate biological reagent with a quantifiable label. Such a label may be radioactive, fluorescent, luminescent, or absorptive of electromagnetic radiation, and the detectable complex may be quantified by a variety of methods known in the art.

The nucleic acids, protein and antibodies of the invention advantageously enable detection and measurement of cellular proliferation in biological fluids, cultured cells and tissues, and are particularly useful for the specific detection of G2 and M-phase cells. Moreover, the isolated CENP-F protein of the invention is useful for detecting autoantibodies to the protein, which may provide an early indication of malignant disease.

DETAILED DESCRIPTION OF THE INVENTION

Figure 1:
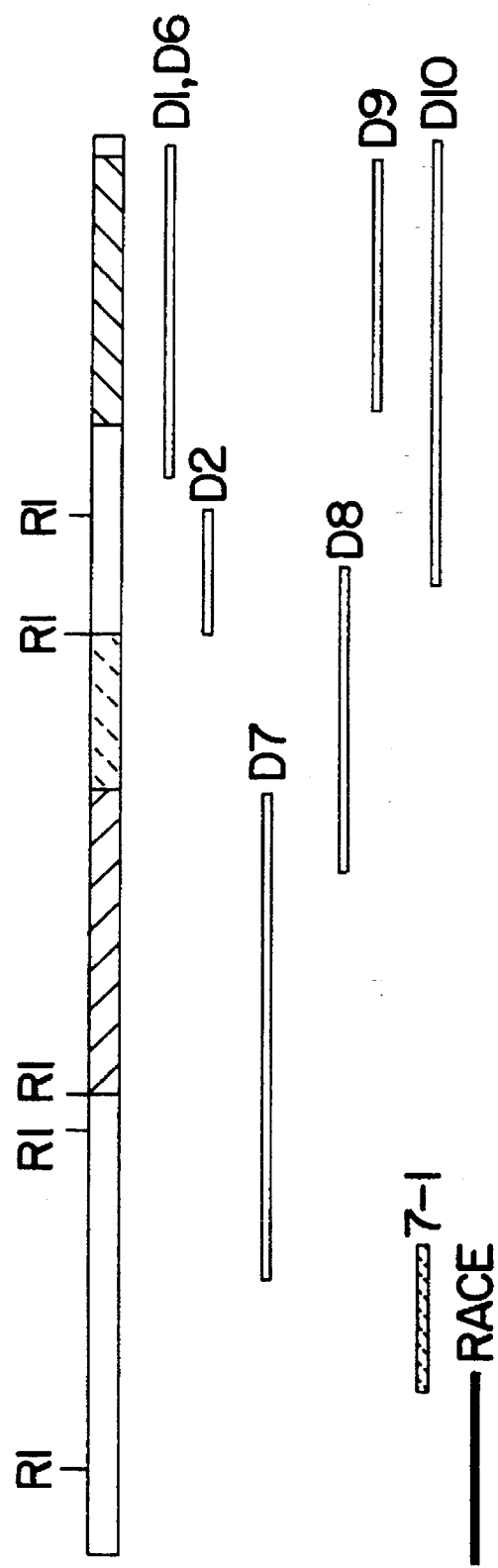
FIG. 1 is a schematic diagram of the human CENP-F-encoding cDNA clone having Sequence I.D. Number 2. The upper of portion of the Figure depicts the full-length cDNA; stippled and hatched regions of the full-length cDNA denote fragments used for expression of protein; "RI" denotes EcoRI restriction sites. The lower portion of the Figure depicts cDNA fragments (D1–D10, 7–1)isolated by antibody screening of expression libraries or synthesized in 5' extension reactions (RACE).

In accordance with the present invention, we have produced a nucleic acid molecule having a sequence that encodes human CENP-F, a novel kinetochore protein recently identified by immunological reaction with an autoimmune serum (Rattner, et al., 1993, supra). Analysis of the nucleotide sequence of a 10.1 kb human cDNA encoding CENP-F revealed that it encodes a 372 kDa protein comprising epitopes that cross-react with the previously-described autoimmune serum. The protein encoded by the cDNA is referred to herein as Sequence I.D. No. 1. The cDNA is referred to as Sequence I.D. No. 2. Prior to the invention disclosed herein, little was known of the CENP-F protein aside from its approximate molecular weight (.ca 400 kDa) and its cellular distribution at different cell cycle times. The cloning and analysis of a cDNA encoding human CENP-F is described in detail in Example 1.

In accordance with the present invention, analysis of the deduced amino acid sequence of the aforementioned cDNA reveals that the 372 kDa protein encoded by the cDNA does not appear to be homologous to any known proteins. However, the polypeptide exhibits remarkable structural similarity to an emerging SMC family of chromatin compaction proteins (see C. L. Peterson, Cell 79: 389–392, 1994). Similar to other SMC proteins, CENP-F is predicted to possess two large coil domains that flank a central core. However, the notable absence of a conserved helix-loop-helix motif and the location of a conserved P-loop NTP binding site at the carboxyl, rather than the amino, terminus suggests that CENP-F is a distant relative of the SMC family. A more detailed structural description of CENP-F is set forth in Example 1.

Immunofluorescence and expression studies reveal that CENP-F localization and expression are cell cycle dependent. Low levels of CENP-F are detected in G1 but dramatically increase as cells progress toward mitosis, and decrease when cells complete mitosis. Since the synthetic rate of CENP-F increases only moderately at late stages of the cell cycle, the rise in steady-state levels is likely due to the stability of the protein. As described in Example 1, pulse-chase experiments revealed that the half-life of CENP-F is approximately 4.5 hours during late G1 and S phase, but is shortened to less than two hours when cells progress through mitosis. The accelerated decay of CENP-F is coupled to mitotic progression, since the protein is stabilized when cells are blocked from completing mitosis. Amongst the chromosome passenger family, CENP-F appears to bind to kinetochores the earliest. CENP-F appears to be one of the proteins to initiate the formation and maturation of the kinetochore trilaminar plates.

Because of its specific appearance and accumulation in the G2 phase of the cell cycle, CENP-F should prove to be particularly useful as a marker of cellular proliferation. The CENP-F-encoding nucleic acids, recombinant proteins and antibodies thereto described herein are advantageously utilized for the detection and quantitation of CENP-F in tissues and cultured cells, and particularly to identify cells in the G2 phase. Additionally, purified recombinant CENP-F, as described herein, may be labelled and used as a general screen to detect circulating autoantibodies in human patients. As explained in greater detail in Example 2, it appears that the presence of circulating autoantibodies to CENP-F (as well as other cell cycle-dependent proteins) may provide an early indication of malignant disease.

The CENP-F-encoding cDNA having Sequence I.D. No. 2 was constructed by repeated antibody probing of a human breast carcinoma cDNA expression library. Allelic variants and natural mutants of Sequence I.D. No. 2 are likely to exist within the human genome and within the genomes of other species. Because such variants are expected to possess certain differences in nucleotide and amino acid sequence, this invention provides an isolated nucleic acid molecule and an isolated CENP-F protein having at least about 50–60% sequence homology in the coding region with the nucleotide sequence set forth as Sequence I.D. No. 2 (and, preferably, specifically comprising the coding region of sequence I.D. No. 2), and the amino acid sequence of Sequence I.D. No. 1. Because of the natural sequence variation likely to exist among CENP-F proteins and nucleic acids encoding them, one skilled in the art would expect to find up to about 40–50% sequence variation, while still maintaining the unique properties of the CENP-F protein of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention. For purposes of this invention, the term "substantially the same" refers to nucleic acid or amino acid sequences having sequence variation that do not materially affect the nature of the protein (i.e. the structure and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning,* Cold Spring Harbor Laboratory (1989) (hereinafter "Sambrook et al.") are used.

I. Preparation of nucleic acid molecules, CENP-F proteins and antibodies thereto A. Nucleic Acid Molecules Nucleic acid molecules encoding CENP-F proteins of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 2, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 10.1-kb double-stranded DNA molecule may be synthesized as several smaller segments of appropriate complementarily. Complementary segments thus produced may be annealed such that each segment possesses appropriate cohesive termini for attachment of an adjacent segment. Adjacent segments may be ligated by annealing cohesive termini in the presence of DNA ligase to construct an entire 10.1-kb double-stranded molecule. A synthetic DNA molecule so constructed may then be cloned and amplified in an appropriate vector.

Nucleic acid sequences encoding CENP-F may be isolated from appropriate biological sources using methods known in the art. In a preferred embodiment, a cDNA clone is isolated from an expression library of human origin. In an alternative embodiment, human genomic clones encoding CENP-F may be isolated. Alternatively, cDNA or genomic clones encoding CENP-F from other species may be obtained.

In accordance with the present invention, nucleic acids having the appropriate level sequence homology with the protein coding region of Sequence I.D. No. 2 may be identified by using hybridization and washing condition of appropriate stringency. For example, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37°–42° C. for at least six hour. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42°–65° in 1×SSC and 1% SDS, changing the solution every 30 minutes.

Nucleic acids of the present invention may be maintained as DNA in any convenient cloning vector. In a preferred embodiment, clones are maintained in plasmid cloning/ expression vector, such as pBluescript (Stratagene, La Jolla, Calif.), which is propagated in a suitable *E. coli* host cell.

CENP-F-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 2. Such oligonucleotides are useful as probes for detecting CENP-F genes in test samples, e.g. by PCR amplification, or as potential regulators of gene expression.

B. Proteins

A full-length CENP-F protein of the present invention may be prepared in a variety of ways, according to known methods. The protein may be purified from appropriate sources, e.g., human or animal cultured cells or tissues, by immunoaffinity purification using autoimmune serum. However, due to the limited amount of CENP-F present in a sample at any given time, conventional purification techniques are not preferred in the present invention.

The availability of nucleic acids molecules encoding CENP-F enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of CENP-F may be produced by expression in a suitable procaryotic or eucaryotic system. For example, part or all of a DNA molecule, such as the cDNA having Sequence I.D. No. 2, may be inserted into a plasmid vector adapted for expression in a bacterial cell, such as E. coli, or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences. An example of a useful procaryotic expression vector for expressing DNA molecules of the invention is described in Example 1.

The CENP-F produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/ secretion vectors are not used, an alternative approach involves purifying the recombinant protein by affinity separation, such as by immunological interaction with antibodies that bind specifically to the recombinant protein. Such methods are commonly used by skilled practitioners.

The CENP-F proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward CENP-F may be prepared according to standard methods (see Example 1). In a preferred embodiment, monoclonal antibodies are prepared, which react immunospecifically with various epitopes of CENP-F. Monoclonal antibodies may be prepared according to general methods of Köhler and Milstein, following standard protocols. Polyclonal or monoclonal antibodies that immunospecifically interact with CENP-F can be utilized for identifying and purifying such proteins. For example, antibodies may be utilized for affinity separation of proteins with which they immunospecifically interact. Antibodies may also be used to immuoprecipitate proteins from a sample containing a mixture of proteins and other biological molecules. Other uses of anti-CENP-F antibodies are described below.

II. Uses of CENP-F-Encoding Nucleic Acids, CENP-F Proteins and Antibodies Thereto Cell proliferative activity has recently received a great deal of attention as a prognostic indicator of neoplastic disease. The measurement of tumor cell proliferation in particular yields a variety of useful data for tumor diagnosis, classification and prognosis. Accordingly, cell cycle-specific markers have become increasingly valuable for clinical and pathological applications. Because CENP-F is specifically detected mainly in the G2 and M phases of the cell cycle, CENP-F promises to be a particularly useful cell cycle-specific marker for assessing proliferative activity in various biological samples.

A. CENP-F-Encoding Nucleic Acids

CENP-F-encoding nucleic acids may be used for a variety of purposes in accordance with the present invention. For monitoring cellular proliferation in vitro or in vivo, CENP-F-encoding DNA, RNA, or fragments thereof, may be used as probes to detect the presence and/or expression of genes encoding CENP-F. Methods in which CENP-F-encoding nucleic acids may be utilized as probes for assays of cellular proliferation include, but are not limited to: (1) in situ hybridization; (2) Southern hybridization; (3) Northern hybridization; and (4) assorted amplification reactions, such as polymerase chain reaction (PCR).

The CENP-F-encoding nucleic acids of the invention may also be utilized as probes to identify related genes either from humans or from other species. As is well known in the art, hybridization stringencies may be adjusted so as to allow hybridization of nucleic acid probes with complementary sequences of varying degrees of homology. Thus, CENP-F-encoding nucleic acids may be used to advantage to identify and characterize other genes, of varying degrees of relation to CENP-F, which may encode proteins functioning in cell division.

As described above, CENP-F-encoding nucleic acids are also used to advantage to produce large quantities of substantially pure CENP-F protein, or selected portions thereof. Due to the scarcity of CENP-F protein in biological tissues at any given time, expressible cDNA encoding CENP-F provide a much-needed source of the protein for use as a diagnostic tool to assess cellular proliferation.

B. CENP-F Protein and Antibodies

As discussed above, and in greater detail in Example 2, studies on human patients have indicated that a relationship may exist between the presence of autoantibodies to CENP-F and diseases involving malignancy. Accordingly, purified CENP-F also may be labelled and used as a sensitive detection reagent to detect the presence and amount of anti-CENP-F autoantibodies from a blood or tissue sample of patients suspected of having a malignancy-related disease.

Purified CENP-F, or fragments thereof, may be used to produce polyclonal or monoclonal antibodies which themselves may serve as sensitive detection reagents for the presence and accumulation of CENP-F in cultured cells or in tissues from living patients. Recombinant techniques enable expression of fusion proteins containing part or all of the .ca 372 kDa CENP-F protein. The full-length protein or fragments of the protein may be used to advantage to generate an array of monoclonal antibodies specific for various epitopes of the protein, thereby potentially providing even greater sensitivity for detection of the protein in cells or tissues.

Polyclonal or monoclonal antibodies immunologically specific for CENP-F may be use in a variety of assays designed to measure cellular proliferation and thereby diagnose or render a prognosis as to a malignant disease. Such assays include, but are not limited to: (1) flow cytometric analysis; (2) immunochemical localization of CENP-F in cultured cells or tissues; and (3) immunoblot analysis (e.g., dot blot, Western blot) of extracts from various cells and tissues. Additionally, as described above, anti-CENP-F antibodies can be used for purification of CENP-F (e.g., affinity column purification, immunoprecipitation).

From the foregoing discussion, it can be seen that CENP-F-encoding nucleic acids, proteins and antibodies thereto can be used to detect CENP-F gene expression, proteins and autoantibodies for purposes of assessing cellular proliferation in a tissue sample. It is expected that these tools will be particularly useful for diagnosis and prognosis of human neoplastic diseases. However, one skilled in the art will appreciate that these tools will also be useful in animal and culture cell experimentation with respect to various malignancies. They can be used to monitor the effectiveness of potential anti-cancer agents on cellular proliferation in vitro, and/or the development of neoplasms or other malignant diseases in animal model systems.

The following examples are provided to describe the invention in further detail. These examples are intended to illustrate and not to limit the invention.

EXAMPLE 1

Cloning and Expression of a cDNA Encoding CENP-F and Analysis of the Recombinant Protein In this example, we describe the cloning of a cDNA molecule encoding human CENP-F, and provide and analysis of the structure of CENP-F as predicted from the deduced amino acid sequence encoded by the cDNA. Additionally, we describe the production of antibodies immunospecific for the recombinant CENP-F protein, and their use in immunological detection of transient expression of CENP-F in synchronously dividing cells.

Materials and Methods

Cell culture and synchronization

HeLa cells were grown at 37° C. in DMEM supplemented with 10% FCS and antibiotics. Synchronization of cells at the G1/S phase was performed by successive thymidine/aphidocolin blocks. Cells were released from the blocks by washing in warm PBS and replacing the growth media. Cell synchrony was monitored by flow cytometry. For pulse labelling, cells were starved in cys⁻ and met⁻ media for 20 minutes before addition of TranSlabel (200 uCi/ml, ICN Biomedicals, Inc., Costa Mesa, Calif.) and 5% dialyzed FCS. Cells were labelled for 10 minutes before harvesting for immunoprecipitations. For pulse-chase experiments, cells that were pre-synchronized at either the G1/S or in G2 were labelled for 30 minutes, washed, and then chased for 1,2, and 4 hours in cold media. Pulse-chase of G2 cells was performed either in the presence of absence of 0.1 µg/ml colcemid (Sigma Chemical Co., St Louis). For BudR labelling, cells that were synchronized at various stages of the cell cycle were incubated in the presence of 10 µM BudR for 15 minutes before processing for detection.

cDNA cloning and sequencing $5 \times 10^5$ phage from a lamdba gt11 human breast carcinoma cDNA expression library (Clontech, Palo Alto, Calif.) was screened with autoimmune serum (Rattner et al., 1993, supra) by following published protocols (Sambrook et al., 1989). Briefly, protein expression was induced by laying IPTG soaked nitrocellulose filters (Millipore Corp., Bedford, Mass.) on the surface of the top agar. After 4 hours at 37° C., filters were removed, rinsed, blocked and incubated overnight at 4° C. with serum (1:500 dilution). Filters were washed the next morning, and bound antibodies were detected with $^{125}$-protein A (ICN). Positive plaques were eluted and rescreened with the autoimmune serum until single plaques were identified. For plaque hybridizations, $3 \times 10^6$ plaques from the same cDNA library were screened with a 300 bp EcoRI and HindIII fragment that was derived from the 5' end of clone D7 (FIG. 1). Probes were labelled to high specific activity with $\alpha^{32}$P dCTP (Amersham, Arlington Heights, Ill.) by random priming. Filters were hybridized at 60° C. in buffer (5×SSPE, 5×Denhardt's, 0.5% SDS, 100 µg/ml of sonicated herring sperm DNA and torula RNA) with 2 to $3 \times 10^6$ cpm/ml of probe. Filters were washed a high stringency (65° C. in 0.2× SSC, 0.1% SDS for 20 minutes) before exposing to X-ray film.

cDNAs were isolated from the recombinant phage DNA by either EcoRI or BsiWI digestion, subcloned into the EcoRI and Acc65I sites respectively, in either the vectors M13 mp18 or pBluescript SK. 5'RACE (Clontech) was performed on HeLA polyA⁺ mRNA to isolate the 5' end of the CENP-F cDNA. To increase specificity, nested primers 5'-CTTTTGCTTTCTCCAGTTGG-3' (Sequence I.D. No. 3) and 5-TTGACGCCTGGTCGTATTG-3', (Sequence I.D. No. 4) respectively were used for the RT-PCR. The complete cDNA was determined from both strands by sequencing overlapping restriction fragments. DNA sequencing was performed with Sequenase v2.0 (U.S. Biochemicals, Cleveland, Ohio). Compilation and analysis of the of the DNA sequences were performed either with MacVector (Kodak, New Haven, Conn.) or GCG (University of Wisconsin).

Northern blots 2 to 3 µg of HeLa polyA⁺mRNA that was isolated from cells enriched in the G2 stage of the cell cycle was separated by agarose gel electrophoresis, transferred onto Hybond N (Amersham) and processed according to manufacturer's instructions. EcoRI fragments derived from each phage clone were used to probe the filters using the hybridization conditions described above.

Expression of bacterial fusion protein and generation of CENP-F antibodies cDNA fragments (derived from clones 7, 8 and 10 shown in FIG. 1) that spanned different portions of CENP-F (from nucleotide 3420 to 6408, 6992 to 7538, and 8445 to end) were subcloned into the EcoRI site of the expression vector pMAL (New England Biolabs, Beverly, Mass.) and transformed into *E. coli* strain CAG456. Protein expression was induced with 1 mM IPTG when cultures reached an O.D. of 0.6. After 4 hours at 30° C., bacteria were harvested, washed and sonicated. The supernatant (S30 fraction) that contained the fusion protein was immediately frozen or boiled in the presence of SDS sample buffer, and the proteins separated by PAGE. Fusion protein was sliced from the gel after staining in 0.1% Coomassie Brilliant Blue and 40% methanol. For immunization, the gel slices were macerated and directly injected into rabbits. Typically, each rabbit was injected with 100 to 200 µg of fusion protein and boosted twice (2 to 3 weeks between boosts) before serum was tested by immunofluorescence staining or immunoblotting. Rabbit IgG was purified by ion exchange chromatography, concentrated by $(NH_2)_2SO_4$ precipitation, dialyzed in PBS and stored at approximately 5 to 10 mg/ml.

Immunodetection methods

For immunofluorescence staining, HeLa cells growing on 18 mm coverslips were fixed at room temperature for 7 minutes in 4% paraformaldehyde buffered in PBS at pH 6.8, extracted for 5 minutes in KB (50 mM Tris-HCl pH 7.4, 150 mM NaCl, 0.1% BSA)+0.2% Triton X-100, rinsed in KB for 10 minutes and then incubated with CENP-F antibodies in a 37° C. humidified chamber. After 30 minutes, coverslips were washed in KB for 10 minutes and re-incubated with biotinylated goat anti-rabbit (1 μg/ml, Gibco BRL, Gaithersburg, Md.) for 30 minutes, followed by incubation in streptavidin-Texas Red and DAPI. If simultaneous detection of bromodeoxyuridine (BrdU) was desirable, the coverslips with the antibody sandwich were re-fixed for 5 minutes in 4% paraformaldehyde/PBS, rinsed in water before submerging into 4M HCl for 10 minutes (the acid treatment also eliminated DAPI staining). After extensive washing, the coverslips were blocked in KB for 10 minutes before incubating with an anti-BrdU monoclonal antibody (1:20, Boerhinger Mannheim Biochemicals). Monoclonal antibody was detected with FITC-coupled goat anti-mouse IgG (10 μg/ml, Gibco). All the samples were mounted in 90% glycerol containing paraphenylenediamine and observed with a Nikon Microphot SA microscope equipped for epifluorescence optics. Images were observed with a 100× Plan Neofluor objective and photographs were recorded on Tmax400 film (Kodak).

Immunoprecipitations were performed by incubating polyclonal CENP-F antibodies (1:200) with HeLa cell lysates at 4° C. for several hours. Immunocomplexes were precipitated with 40 μl of a 1:1 slurry of protein A-sepharose beads (Pharmacia, Picataway, N.J.). Immunoprecipitates were boiled in SDS sample buffer and separated by SDS PAGE. For detection of $^{35}$S-labelled proteins, the gels were fixed and enhanced before exposing to X-ray film (Kodak XAR). For Western blot analysis, the separated proteins in the gels were transferred onto Immobilon P (Millipore), blocked, incubated with anti-CENP-F antibodies as described (Rattner et al., 1993, supra). Bound antibodies were detected with $^{125}$I-protein A (ICN).

Results

Cloning of CENP-F cDNA

We isolated ten immunopositive phage clones (D1 through D10 shown in FIG. 1) after screening a cDNA expression library with the autoimmune serum that contained CENP-F antibodies. Initial restriction mapping and sequence analysis of these clones revealed that they were all related with exception of clone D5 which was not further characterized. Clones D7, D8 and D10 overlapped one another and spanned 8.3 kb of contiguous DNA that included a polyadenylation sequence as well as a homopolyA tract at the 3' end of clone D10. Since all three clones contained multiple EcoRI fragments, we considered whether they might be derived from the same mRNA by using each fragment to probe HeLa polyA$^+$ mRNA by Northern blot analysis. Consistent with this possibility, all of the fragments hybridized to a single, 10 to 11 kb RNA that was of the appropriate size to encode the estimated 400 kDa CENP-F protein.

Exhaustive screening of the DNA library by plaque hybridization yielded a single clone ("7-1" in FIG. 1) that extended the cDNA by about 0.75 kb toward the 5' end. Since the open reading frame that was derived from the 9 kb of contiguous DNA sequences was insufficient to account for full-length CENP-F, 5'RACE was used to attempt to extend the DNA toward the 5' end of the CENP-F mRNA. Based on our finding that the CENP-F mRNA was most abundant during the G2 stage of the cell cycle, we isolated polyA$^+$ mRNA derived from this timepoint and used nested oligonucleotide primers that were near the 5' end of the existing cDNA for RT-PCR. PCR products that extended the cDNA by another 1.1 kb were obtained. DNA sequence of several independent PCR clones revealed that we had isolated two PCR-extension products that differed only in that the 5' end of one fragment was 42 base pairs longer than the other. The shorter PCR product is presumably derived from a prematurely terminated product from the first-strand synthesis reaction. Inspection of the complete 10,130-bp CENP-F cDNA revealed that, if translation initiated at nucleotide position 171, a polypeptide of 3248 amino acids with an estimated mass of 372 kDa would be produced. Given that no extended ORF's were present upstream of this ATG and that the calculated mass is close the estimated size of 400 kDa, we concluded that the complete coding sequence of CENP-F was cloned.

Authentication of the CENP-F cDNA

The authenticity of the initial cDNA clones was also validated. To verify whether the original phage clones encoded CENP-F, three non-overlapping cDNA fragments derived from clones D7, D8 and D10 (FIG. 1) were subcloned into the expression vector pMAL for protein expression in bacteria. Analysis of the proteins expressed after induction revealed that all three fragments expressed a fusion protein of the appropriate size (172 kDa, 82 kDa and 96 kDa) and were recognized by the autoimmune serum. Sera from immunized rabbits that recognized the injected fusion proteins by immunoblot analysis were subsequently tested for their ability to recognize the authentic CENP-F protein. Since identical results were obtained with all three sera, only antibodies raised against the D10 fusion protein were used for subsequent studies. Western blot analysis of HeLa mitotic cell lysates showed that, while the pre-immune antibodies failed to detect a protein of the size of CENP-F, the D10 antibodies identified a large molecular weight protein that shared very similar electrophoretic mobility with authentic CENP-F. Furthermore, the ability of the antibodies to recognize CENP-F-containing immunoprecipitates confirmed that the cDNAs encoded epitopes that are shared with CENP-F.

We next examined the immunofluorescence staining patterns produced by the antibodies in a population of synchronously growing HeLa cells. Pre-immune sera incubated under identical conditions as the immune sera produced only background staining. On the other hand, the D10 antibody produced a staining pattern that was nearly identical with that obtained with the autoimmune serum (Rattner et al, 1993, supra). As was the case for the autoimmune serum, the majority of interphase cells did not exhibit D10 antibody staining that was significantly above background. However, a small percentage (15 to 20%) of interphase cells, presumably at late stages of their cell cycle, exhibited bright nuclear staining. At prophase, when the chromatin begins to condense, a double-dot staining pattern, which probably reflects the staining of the centromere-kinetochore complex, was detected. Staining of the centromere-kinetochore region was most prominent in prometaphase and metaphase. As cells progressed into anaphase, staining of the centromere-kinetochore complex was still detectable, although at reduced intensities. Late in anaphase, staining was relatively diffuse throughout the cell with the exception of a distinct, narrow stripe of staining confined at the spindle equator. The narrow stripe of staining is presumably concentrated to both sides of the midbody as a result of cleavage furrow formation during cytokinesis. The ability of antibodies produced from three non-overlapping regions of the cDNA to produce nearly the identical staining pattern as seen with the autoimmune serum, coupled with their ability to recognized authentic CENP-F by immunoblot analysis, confirms that we had successfully cloned proteins of the CENP-F cDNA.

Structural Analysis of Recombinant CENP-F

Comparison of the primary sequence of CENP-F with either FASTA or BLAST (both publicly available sequence analysis databases) did not reveal any significant homologies with other known proteins. However, CENP-F consistently exhibited a low level of homology (<20%) with the rod domains of many cytoskeletal proteins such as myosins, kinesins, lamins and tropomyosins that probably reflects similarities in secondary structure. Analysis of the CENP-F amino acid sequence with the COILS2 program (public software) revealed that residues 1 to 200, 280 to 1350, 1620 to 1750, 1850 to 2990 exhibited high probabilities of forming an extended coiled structure. Located in between the two largest coil domains, from 1380 to 1610, is a putative globular domain that consists of two direct repeats of 95 amino acids. The COOH-terminal 200 amino acids is predicted to form a globular domain that is highly basic (pI of 10) and proline-rich(10.6%). Consistent with its nuclear localization, several consensus nuclear localization sequences are found within the $NH_2$ and COOH-terminal 200 amino acids. Additionally, clusters of consensus phosphorylation sites for either MAP kinases or cyclin-dependent kinases (cdk) are present within both the terminal domains. Finally, a consensus P-loop nucleotide binding site (A/GXXXXGKS/T) is located within the COOH terminus.

The general organization of the CENP-F protein is highly similar to the newly discovered SMC family of chromatin compaction proteins. The SMC proteins have two long extended coil domains that flank a central core domain. Within the $NH_2$ terminal domains of the SMC family members, there is a conserved P-loop consensus, as well as similarity within the surrounding 59 residues. Likewise, SMC family members share a helix-loop-helix domain within the COOH terminus.

Although CENP-F protein does not appear to exhibit any significant sequence homologies with other known proteins, its predicted secondary structure reveals a tripartite organization consisting of a head, extended rod and tail domains that bears striking resemblance to the SMC family of chromosome condensation proteins. Like all SMC family members, the central domain of CENP-F consists of two extended coil-coil domains that are separated by a spacer region. Although CENP-F possesses a NTP-binding site that is conserved amongst all the SMC family members, it is located within its COOH-terminal globular domain instead of at the $NH_2$ terminus. This difference, coupled with the absence of a conserved helix-loop-helix domain in CENP-F suggests that it may be only a distant relative of the SMC family.

Analysis of CENP-F expression during the cell cycle

Previous data as well as the results reported here show that CENP-F is a nuclear protein that is detected in only some interphase cells. To monitor when CENP-F is detectable during the cell cycle, we stained HeLa cells that were synchronized at different portions of the cell cycle. Examination of early G1 cells that were obtained several hours after replating a population of mechanically disloged mitotic cells did not produce detectable levels of CENP-F. Likewise, CENP-F was not detectable in cells that were arrested at the G1/S boundary. One hour after releasing cells from the G1/S boundary, faint CENP-F staining was detected in the nuclei that were replicating DNA as monitored by BrdU incorporation. Staining intensity increased gradually as cells progressed through S phase and reached the brightest levels during G2.

To obtain quantitative data on the cell cycle expression pattern of CENP-F, we measured the steady-state levels of CENP-F in cells that were synchronized at various parts of the cell cycle. Consistent with the absence of CENP-F staining in G1 cells, immunoblot analysis did not detect CENP-F in cells that were synchronized at the G1/S boundary. CENP-F steady-state levels gradually accumulated as cells progressed through S phase and reached peak levels at G2 and M. Steady-state levels dropped dramatically when cells completed mitosis and reentered G1. Consistent with the increase in the steady-state levels, there was a moderate increase in the synthesis rate of CENP-F between cells blocked at the G1/S boundary and G2 cells. We compared the turnover rate of CENP-F at different points in the cell cycle to determine whether there was an accelerated decay of CENP-F in cells progressing through mitosis. The average $t^{1/2}$ was reduced to approximately 1.8 hours. This is likely still an overestimate since the last time point in G1 commonly is contaminated with a small (~15%) but significant fraction of mitotic cells that contain stable pulse-labelled CENP-F. In a parallel pulse-labelled culture that was blocked from completing mitosis by chasing them in media containing colcemid, CENP-F was undegraded. Thus, the accelerated degradation of CENP-F is dependent upon the cells' ability to progress through mitosis.

EXAMPLE 2

Association of Circulating CENP-F AutoAntibodies with Malignancy and Assessment of CENP-F Distribution in Malignant and Non-Malignant Tissues The mammalian centromere is a multi-functional chromosomal domain that plays a major role during cell proliferation mediating both chromosome movement and sister chromatid association. Six unique mammalian CENtromere Proteins (CENP) have been identified and at least five (CENP A, B, C, D and F) are target antigens in autoimmune diseases. Of the six centromere proteins, four (CENP-A, B, C, and D) are found in association with the centromere throughout the cell cycle. The remaining two (CENP-E and F), are found only at the centromere during the latter stages of the cell cycle. The ability of CENP-F antibodies to allow the specific detection of G2 and M-phase cells in tissue culture cells enables CENP-F to be a useful addition to the list of cell cycle specific markers used to study cell proliferation in tumor samples.

The studies set forth in this Example were undertaken to gather more information about the relationship between individuals possessing autoantibodies to CENP-F and the development of malignant disease, and to determine if this antigen is present in malignant tissues.

Materials and Methods

Serum and Clinical Information Collection

Eight sera containing autoantibodies to CENP-F were first detected by indirect immunofluorescence using a commercially available Hep-2 cell substrate (Immuno Concepts Inc., Sacramento, Calif.). These sera displayed a typical pattern of CENP-F staining. Reactivity within the .ca 400 kDa region of immunoblots was confirmed using HeLa cell protein, following the procedure described by Rattner et al., 1993, supra. The clinical information was obtained retrospectively.

Specimen Collection

Cryopreserved tissue samples were collected through the Histopathology Department of the Foothills Hospital, Calgary, Alberta, Canada from unselected patients undergoing radical mastectomy or reduction mammoplasty. All breast cancer specimens described herein were determined to have ductual carcinoma using standard pathological criteria. Specimens of tonsil were collected from routine tonsillectomies. Samples were quick frozen and frozen section were cut and stored at −20° C. until use.

Two cell lines of breast tumor origin (HTB 30 and HTB 132), originally obtained from the American Type Tissue Collection, were a gift from Drs. Don Fujita and Karl Riabowol, The University of Calgary. Both HTB 30 and HTB 132 were derived from a breast adenocarcinoma. The cells were grown in Joklik's suspension medium supplemented with 10% fetal calf serum. Forty-eight hours prior to use, cells were seeded onto coverslips.

Indirect Immunofluorescence (IIF)

Frozen sections or monolayer cultures of tissue culture cells grown on coverslips were fixed for 10 minutes in 3% paraformaldehyde in Dulbecco's phosphate buffered saline (D-PBS). Fixed preparation were washed in D-PBS and then incubated for 1 hour at 37° C. in a 1:100 dilution of a CENP-F antiserum, as described by Rattner et al., 1993 supra. For double label experiments, specimens were incubated in a mixture of the CENP-F serum at a dilution of 1:100 and commercially available mouse monoclonal antibody to Ki-67 (Dakopatts) at a dilution of 1:50. In some experiments a human autoimmune serum containing antibodies to the centrosome were used at a dilution of 1:50. The characterization of this serum has been previously reported (Rattner, et al., J. Immunol. 146: 2341-2344, 1991).

Following three washes in D-PBS, the samples were incubated for one hour at 37° C. in secondary antibody: fluorescein conjugated anti-human IgG(H+L) (Dakopatts) and/or a rhodamine conjugated anti-mouse IgG(H+L) (Dakopatts). After incubation, the specimens were washed in D-PBS, counterstained with DAPI (4',6-diamindino-2-phenylidole), and mounted in 90% glycerol containing paraphenylenediamine and observed using a Nikon Optophot flourescence microscope. Images were recorded on Ilford HP-5 film.

Immunoblotting

Imunoblotting was performed on nitrocellulose strips containing proteins from a breast tumor sample and cells harvested from log phase cultures of HTB 30 and HTB 132 cultures. Proteins from cell lysates ware separated by 4% SDS polyacrylamide gel electrophoresis. The whole cell protein extracts used for the immunoblots were obtained by suspending tissue fragments or tissue culture cells detached from monolayer cultures by trypsin digestion in SDS sample buffer, followed by sonication. Antibody binding to nitrocellulose strips was detected using enhanced chemiluminescence (ECL, Amersham). The anti-CENP-F serum was used at a dilution of 1:100.

RESULTS

The clinical diagnosis and demographic features of 8 patients with antibodies to CENP-F are shown in Table 1.

TABLE 1

Clinical Features of Patients with CENP-F Antibodies

| Patient | Age | Gender | Primary Complaints | Diagnosis |
|---|---|---|---|---|
| 1 | 72 | F | Fever | Prolactinoma, Hepatitis |
| 2 | 72 | F | Arthralgia | BRC |
| 3 | 75 | M | Fever, arthritis | SCLC |
| 4 | 58 | M | Arthritis, dyspnea | SCLC |
| 5 | 50 | F | Arthritis, fever | OVC |
| 6 | 64 | M | Arthritis, vasculitis | SCLC |
| 7 | 76 | F | Arthralgia, Myalgia, hemoptysis | BRC |
| 8 | 46 | F | Arthralgia | None |

Abbreviations: BRC = breast carcinoma, OvC ovary carcinoma, SCLC-small cell lung carcinoma.

As shown in Table 1, three patients were males and 5 were females. The age range was 46 to 76 years (mean 64 years). Four patients presented with complaints of arthritis but did not fulfill the American College of Rheumatology criteria for rheumatoid arthritis. Other patients' symptoms included fever of unknown origin (n=3), arthralgia (n=3), myalgia (n=1), hemoptysis (n=1) and dyspnea (n=1). Six patients were subsequently found to have a malignancy. Four had small cell lung carcinoma, two had carcinoma of the breast and one carcinoma of the ovary. One patient had a prolactinoma and abnormal liver function tests but did not have laboratory evidence for infectious disease. One patient had a retinal vasculitis and another patient did not have a definitive diagnosis.

The presence of autoantibodies to CENP-F in patients with carcinomas raised the question of the possible source of the autoantigen. To determine if CENP-F is expressed in proliferating cells of tumor and/or nontumor origin, we first reacted CENP-F antibodies with a frozen section of tonsil (as an example of nontumor tissue) and counterstained for DNA with DAPI. Reactivity was detectable in small population of cells. In this population, reactivity was either seen throughout the nucleus, a pattern characteristic of G2 cells, or as a series of paired punctuate spots in regions containing clusters of chromosomes. Cells in the latter stages of cell division were not observed in our tissue samples.

Since some individuals in the CENP-F patient group had breast carcinoma, and since breast tumor tissue and breast cancer cell lines were readily available, we chose this tumor type as a prototype to study CENP-F distribution in malignant tissue. For comparative purposes, CENP-F antibodies were first reacted with monolayers of two breast carcinoma cell lines, HTB-30 and HTB-132, and examined by IIF. Both cells lines showed a pattern of reactivity similar to that documented for CENP-F in HeLa and Hep-2 cell lines. That is, within the reactive cell population, several types of patterns could be detected. In the first, reactivity was seen throughout intact nuclei. Cells with maximum reactivity displaying this IIF pattern were double stained with antibodies to the centrosome; these cells displayed duplicated and separated centrosomes. This pattern is characteristic of cells in the G2-M-phase transition. The second pattern of CENP-F reactivity was confined to cells that displayed recognizable chromosomes. In these cells, the CENP-F reactivity was confined to small punctate regions and generally appeared as paired spots. Finally, examination of anaphase and telophase cells revealed the final relocation of the CENP-F antigen to the spindle midzone in a region lateral to the midbody. Western blot analysis of proteins derived from both breast cancer cell lines using the CENP-F serum confirmed the presence of the CENP-F antigen.

To determine the percent of actively proliferating cells displaying detectable CENP-F antigen, in breast cancer cells line as compared to HeLa cells, five-hundred cells were scored for both Ki-67 and CENP-F reactivity. Monolayer cultures that had reached semi-confluency 48 hours after plating onto coverslips were used for each cell line. Results are shown in Table 2.

TABLE 2

| Cell Type | % Ki-67 reactive cells | % CENP-F reactive cells | % Ki-67 cells also reactive with CENP-F |
|---|---|---|---|
| HeLa | 91% | 9% | 9% |
| HTB-30 | 46% | 9% | 18% |
| HTB-132 | 87% | 13% | 15% |

As shown in Table 2, strongly staining CENP-F reactive cells represent a small subpopulation of cycling cells within each cell line as indicated by Ki-67 reactivity. The proportion of this population is similar in the cell lines of breast cancer origin, irrespective of the percent of cycling cells, and is greater than that found in HeLa cells. In all cell lines, CENP-F reactive cells were always found to be Ki-67 positive.

To determine if the CENP-F pattern seen in the breast carcinoma cell lines was also detectable in tumor tissue samples, double label experiments were carried out using antibodies to Ki-67 and CENP-F on cryopreserved sections of breast cancer tissue counterstained with DAPI. When detected, CENP-F reactive cells represented a minor population of Ki-67 reactive cells seen within a variety of tumor samples. In many samples abundant Ki-67 cells were observed, with no detectable CENP-F population.

Within samples displaying CENP-F reactive cells, two distinct patterns of reactivity were seen. In the first, CENP-F reactivity was found throughout the nucleus, a pattern characteristic of G2 cells. In the second, the CENP-F pattern appeared punctate. In cells displaying this pattern, the corresponding DAPI image revealed distinct chromosomes and the corresponding Ki-67 images displayed a halo pattern characteristic of the prometaphase-metaphase staining pattern produced by this antibody due to its localization to the surface of the chromosome. Neither Ki-67 nor CENP-F reactive cells were observed in cryosection of tissue obtained from reduction mammoplasties.

The number and pattern of Ki-67 and CENP-F reactive cells varied both between tissue samples and within regions of a single section. In some regions, or samples, CENP-F reactive cells occurred singly, while in others, clusters of positive cells could be detected which generally displayed the G2 pattern of reactivity. When samples displaying clusters of CENP-F reactive cells were stained with anti-centrosome antibodies, it was possible to observe duplicated and separated centrosomes adjacent to the reactive nuclei. This centrosomal pattern was consistent with the suggestion made by the CENP-F pattern that these cells are in the latter stages of the cell cycle immediately preceding mitosis. We were unable to detect CENP-F in Western blots prepared from tissue samples showing CENP-F reactivity by IIF. This likely reflects the relatively small population of cells expressing CENP-F in the total cell population present in the tissue sample.

Discussion

All of the patients described in this Example sought medical advice after the onset of constitutional rheumatic disease symptoms and ⁶/₈ were subsequently found to have a malignancy. In the last decade, there has been a growing interest in autoantibodies in malignancy, some of which are used as markers of paraeoplastic syndromes. For example, antibodies to the cytoplasmic antigen Yo serve as a marker for paraneoplastic cerebellar degeneration in patients with breast or ovarian cancer (Peterson et al., Neurology 42: 1931–1937, 1992). Antibodies to the nuclear antigen Hu are a marker for paraneoplastic encephalomyelitis in patients with small cell lung cancer and other malignancies (Dalmau et al., Ann. Neurol. 27 544–552, 1990). The pattern of staining and the molecular weight of the CENP-F antigen distinguish it from previously described autoantibodies associated with paraneoplastic syndromes.

It is clear from numerous studies of cancer that there is a relationship between the degree of cellular proliferation and prognosis, and this is also true in the case of mammary carcinomas. In general, higher proliferation rates are found in malignant tumors and only rarely in benign tumors. In malignant tumors, high proliferation rates are associated with a poorer prognosis and response to radiotherapy or chemotherapy than neoplasms with lower proliferation rates. Mitotic counts from conventional hematoxylin and eosin sections have enjoyed the most general acceptance for the determination of proliferation in surgical pathology. However, this approach has the drawback that such counts may be subjective and may not be reproducible. In addition, fixation of sections can affect the number of mitoses observed.

In contrast to other procedures, immunohistochemical procedures offer the advantage of negligible tissue consumption and of in situ analysis which allows differentiation of proliferating tumor cells from stromal cell populations. Recently, a number of markers of cell proliferation useful in detecting and quanititating proliferating cells have been described. These markers generally react with cells throughout the cell cycle and do not allow one to distinguish specific stages in the cell cycle with ease. In the present study we provide evidence that a cell cycle-specific centromere protein, CENP-F, allows the direct visualization and discrimination of a subpopulation of cycling cells (G2 and M-phase populations) in frozen section of normal and malignant tissues. The availability of this probe makes it possible to extract precise cell cycle information directly from cytological specimens.

While certain embodiments of the present invention have been described and exemplified above as preferred embodiments, various other embodiments should be apparent to those skilled in the art from the foregoing disclosure. The present invention, therefore, is not limited to the embodiments specifically described and exemplified above, but is capable of variation and modification within the scope of the appended claims.

What is claimed is:

1. An isolated, purified nucleic acid molecule that encodes a human kinetochore protein transiently expressed during G2 and M phases of a cell cycle, said protein having a molecular weight between about 340 kD and 420 kD, said protein having a general structure comprising two extended coil domains flanking a non-coil core domain, at least one nuclear localization consensus signal at the amino terminus, a conserved P-loop nucleotide binding site at the carboxyl terminus, and lacking the conserved helix-loop-helix domain characteristic of the SMC family of chromosome condensation proteins.

2. The nucleic acid molecule of claim 1, wherein said sequence encodes a polypeptide approximately 3,248 amino acids in length.

3. The nucleic acid of claim 1, which is RNA.

4. The nucleic acid of claim 1, which is DNA.

5. An isolated and purified nucleic acid molecule which encodes a polypeptide having the amino acid sequence of SEQ ID NO: 1.

6. The nucleic acid of claim 5, which has the sequence of SEQ ID NO: 2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3248 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: HUMAN ( x i ) SEQUENCE DESCRIPTION: SEQ ID NO:1:

```
Met Ser Trp Ala Leu Glu Glu Trp Lys Glu Gly Leu Pro Thr Arg Thr
 1               5                  10                  15

Leu Gln Lys Ile Gln Glu Leu Glu Gly Gln Leu Asp Lys Leu Lys Lys
            20                  25                  30

Glu Lys Gln Gln Arg Gln Phe Gln Leu Asp Ser Leu Glu Ala Ala Pro
        35                  40                  45

Gln Lys Gln Thr Gln Lys Val Glu Asn Glu Lys Thr Glu Gly Thr Asn
    50                  55                  60

Leu Lys Arg Glu Asn Gln Arg Leu Met Glu Ile Cys Glu Ser Leu Glu
65                  70                  75                  80

Lys Thr Lys Gln Lys Ile Ser His Glu Leu Gln Val Lys Glu Ser Gln
                85                  90                  95

Val Asn Phe Gln Glu Gly Gln Leu Asn Ser Gly Lys Lys Gln Ile Glu
                100                 105                 110

Lys Leu Glu Gln Glu Leu Lys Arg Cys Lys Ser Glu Leu Glu Arg Ser
            115                 120                 125

Gln Gln Ala Ala Gln Ser Ala Asp Val Ser Leu Asn Pro Cys Asn Thr
        130                 135                 140

Pro Gln Lys Ile Phe Thr Thr Pro Leu Thr Pro Ser Gln Tyr Tyr Ser
145                 150                 155                 160

Gly Ser Lys Tyr Glu Asp Leu Lys Glu Lys Tyr Asn Lys Glu Val Glu
                165                 170                 175

Glu Arg Lys Arg Leu Glu Ala Glu Val Lys Ala Leu Gln Ala Lys Lys
            180                 185                 190

Ala Ser Gln Thr Leu Pro Gln Ala Thr Met Asn His Arg Asp Ile Ala
        195                 200                 205

Arg His Gln Ala Ser Ser Val Phe Ser Trp Gln Gln Glu Lys Thr
    210                 215                 220

Pro Ser His Leu Ser Ser Asn Ser Gln Arg Thr Pro Ile Arg Arg Asp
225                 230                 235                 240

Phe Ser Ala Ser Tyr Phe Ser Gly Glu Leu Glu Val Thr Pro Ser Arg
                245                 250                 255

Ser Thr Leu Gln Ile Gly Lys Arg Asp Ala Asn Ser Ser Phe Phe Gly
            260                 265                 270

Asn Ser Ser Ser Pro His Leu Leu Asp Gln Leu Lys Ala Gln Asn Gln
        275                 280                 285
```

```
Glu  Leu  Arg  Asn  Lys  Ile  Asn  Glu  Leu  Glu  Leu  Arg  Leu  Gln  Gly  His
     290                 295                      300
Glu  Lys  Glu  Met  Lys  Gly  Gln  Val  Asn  Lys  Phe  Gln  Glu  Leu  Gln  Leu
305                      310                      315                      320
Gln  Leu  Glu  Lys  Ala  Lys  Val  Glu  Leu  Ile  Glu  Lys  Glu  Lys  Val  Leu
                    325                      330                      335
Asn  Lys  Cys  Arg  Asp  Glu  Leu  Val  Arg  Thr  Thr  Ala  Gln  Tyr  Asp  Gln
               340                      345                      350
Ala  Ser  Thr  Lys  Tyr  Thr  Ala  Leu  Glu  Gln  Lys  Leu  Lys  Lys  Leu  Thr
          355                      360                      365
Glu  Asp  Leu  Ser  Cys  Gln  Arg  Gln  Asn  Ala  Glu  Ser  Ala  Arg  Cys  Ser
     370                      375                      380
Leu  Glu  Gln  Lys  Ile  Lys  Glu  Lys  Glu  Lys  Glu  Phe  Gln  Glu  Glu  Leu
385                      390                      395                      400
Ser  Arg  Gln  Gln  Arg  Ser  Phe  Gln  Thr  Leu  Asp  Gln  Glu  Cys  Ile  Gln
               405                      410                      415
Met  Lys  Ala  Arg  Leu  Thr  Gln  Glu  Leu  Gln  Gln  Ala  Lys  Asn  Met  His
               420                      425                      430
Asn  Val  Leu  Gln  Ala  Glu  Leu  Asp  Lys  Leu  Thr  Ser  Val  Lys  Gln  Gln
          435                      440                      445
Leu  Glu  Asn  Asn  Leu  Glu  Glu  Phe  Lys  Gln  Lys  Leu  Cys  Arg  Ala  Glu
     450                      455                      460
Gln  Ala  Phe  Gln  Ala  Ser  Gln  Ile  Lys  Glu  Asn  Glu  Leu  Arg  Arg  Ser
465                      470                      475                      480
Met  Glu  Glu  Met  Lys  Lys  Glu  Asn  Asn  Leu  Leu  Lys  Ser  His  Ser  Glu
               485                      490                      495
Gln  Lys  Ala  Arg  Glu  Val  Cys  His  Leu  Glu  Ala  Glu  Leu  Lys  Asn  Ile
               500                      505                      510
Lys  Gln  Cys  Leu  Asn  Gln  Ser  Gln  Asn  Phe  Ala  Glu  Glu  Met  Lys  Ala
          515                      520                      525
Lys  Asn  Thr  Ser  Gln  Glu  Thr  Met  Leu  Arg  Asp  Leu  Gln  Glu  Lys  Ile
     530                      535                      540
Asn  Gln  Gln  Glu  Asn  Ser  Leu  Thr  Leu  Glu  Lys  Leu  Lys  Leu  Ala  Val
545                      550                      555                      560
Ala  Asp  Leu  Glu  Lys  Gln  Arg  Asp  Cys  Ser  Gln  Asp  Leu  Leu  Lys  Lys
                    565                      570                      575
Arg  Glu  His  His  Ile  Glu  Gln  Leu  Asn  Asp  Lys  Leu  Ser  Lys  Thr  Glu
               580                      585                      590
Lys  Glu  Ser  Lys  Ala  Leu  Leu  Ser  Ala  Leu  Glu  Leu  Lys  Lys  Lys  Glu
          595                      600                      605
Tyr  Glu  Glu  Leu  Lys  Glu  Glu  Lys  Thr  Leu  Phe  Ser  Cys  Trp  Lys  Ser
     610                      615                      620
Glu  Asn  Glu  Lys  Leu  Leu  Thr  Gln  Met  Glu  Ser  Glu  Lys  Glu  Asn  Leu
625                      630                      635                      640
Gln  Ser  Lys  Ile  Asn  His  Leu  Glu  Thr  Cys  Leu  Lys  Thr  Gln  Gln  Ile
               645                      650                      655
Lys  Ser  His  Glu  Tyr  Asn  Glu  Arg  Val  Arg  Thr  Leu  Glu  Met  Asp  Arg
               660                      665                      670
Glu  Asn  Leu  Ser  Val  Glu  Ile  Arg  Asn  Leu  His  Asn  Val  Leu  Asp  Ser
          675                      680                      685
Lys  Ser  Val  Glu  Val  Glu  Thr  Gln  Lys  Leu  Ala  Tyr  Met  Glu  Leu  Gln
     690                      695                      700,
```

```
Gln Lys Ala Glu Phe Ser Asp Gln Lys His Gln Lys Glu Ile Glu Asn
705                 710                 715                 720

Met Cys Leu Lys Thr Ser Gln Leu Thr Gly Gln Val Glu Asp Leu Glu
                725                 730                 735

His Lys Leu Gln Leu Leu Ser Asn Glu Ile Met Asp Lys Asp Arg Cys
            740                 745                 750

Tyr Gln Asp Leu His Ala Glu Tyr Glu Ser Leu Arg Asp Leu Leu Lys
        755                 760                 765

Ser Lys Asp Ala Ser Leu Val Thr Asn Glu Asp His Gln Arg Ser Leu
    770                 775                 780

Leu Ala Phe Asp Gln Gln Pro Ala Met His His Ser Phe Ala Asn Ile
785                 790                 795                 800

Ile Gly Glu Gln Gly Ser Met Pro Ser Glu Arg Ser Glu Cys Arg Leu
                805                 810                 815

Glu Ala Asp Gln Ser Pro Lys Asn Ser Ala Ile Leu Gln Asn Arg Val
            820                 825                 830

Asp Ser Leu Glu Phe Ser Leu Ser Gln Lys Gln Met Asn Ser Asp
        835                 840                 845

Leu Gln Lys Gln Cys Glu Glu Leu Val Gln Ile Lys Gly Glu Ile Glu
    850                 855                 860

Glu Asn Leu Met Lys Ala Glu Gln Met His Gln Ser Phe Val Ala Glu
865                 870                 875                 880

Thr Ser Gln Arg Ile Ser Lys Leu Gln Glu Asp Thr Ser Ala His Gln
                885                 890                 895

Asn Val Val Ala Glu Thr Leu Ser Ala Leu Glu Asn Lys Glu Lys Glu
            900                 905                 910

Leu Gln Leu Leu Asn Asp Lys Val Glu Thr Glu Gln Ala Glu Ile Gln
        915                 920                 925

Glu Leu Lys Lys Ser Asn His Leu Leu Glu Asp Ser Leu Lys Glu Leu
930                 935                 940

Gln Leu Leu Ser Glu Thr Leu Ser Leu Glu Lys Lys Glu Met Ser Ser
945                 950                 955                 960

Ile Ile Ser Leu Asn Lys Arg Glu Ile Glu Glu Leu Thr Gln Glu Asn
                965                 970                 975

Gly Thr Leu Lys Glu Ile Asn Ala Ser Leu Asn Gln Glu Lys Met Asn
            980                 985                 990

Leu Ile Gln Lys Ser Glu Ser Phe Ala Asn Tyr Ile Asp Glu Arg Glu
        995                 1000                1005

Lys Ser Ile Ser Glu Leu Ser Asp Gln Tyr Lys Gln Glu Lys Leu Ile
    1010                1015                1020

Leu Leu Gln Arg Cys Glu Glu Thr Gly Asn Ala Tyr Glu Asp Leu Ser
1025                1030                1035                1040

Gln Lys Tyr Lys Ala Ala Gln Glu Lys Asn Ser Lys Leu Glu Cys Leu
                1045                1050                1055

Leu Asn Glu Cys Thr Ser Leu Cys Glu Asn Arg Lys Asn Glu Leu Glu
            1060                1065                1070

Gln Leu Lys Glu Ala Phe Ala Lys Glu His Gln Glu Phe Leu Thr Lys
        1075                1080                1085

Leu Ala Phe Ala Glu Glu Arg Asn Gln Asn Leu Met Leu Glu Leu Glu
    1090                1095                1100

Thr Val Gln Gln Ala Leu Arg Ser Glu Met Thr Asp Asn Gln Asn Asn
1105                1110                1115                1120

Ser Lys Ser Glu Ala Gly Gly Leu Lys Gln Glu Ile Met Thr Leu Lys
                1125                1130                1135
```

```
Glu Glu Gln Asn Lys Met Gln Lys Glu Val Asn Asp Leu Leu Gln Glu
            1140                1145                1150

Asn Glu Gln Leu Met Lys Val Met Lys Thr Lys His Glu Cys Gln Asn
            1155                1160                1165

Leu Glu Ser Glu Pro Ile Arg Asn Ser Val Lys Glu Arg Glu Ser Glu
            1170                1175                1180

Arg Asn Gln Cys Asn Phe Lys Pro Gln Met Asp Leu Glu Val Lys Glu
1185                1190                1195                1200

Ile Ser Leu Asp Ser Tyr Asn Ala Gln Leu Val Gln Leu Glu Ala Met
            1205                1210                1215

Leu Arg Asn Lys Glu Leu Lys Leu Gln Glu Ser Glu Lys Glu Lys Glu
            1220                1225                1230

Cys Leu Gln His Glu Leu Gln Thr Ile Arg Gly Asp Leu Glu Thr Ser
            1235                1240                1245

Asn Leu Gln Asp Met Gln Ser Gln Glu Ile Ser Gly Leu Lys Asp Cys
            1250                1255                1260

Glu Ile Asp Ala Glu Glu Lys Tyr Ile Ser Gly Pro His Glu Leu Ser
1265                1270                1275                1280

Thr Ser Gln Asn Asp Asn Ala His Leu Gln Cys Ser Leu Gln Thr Thr
            1285                1290                1295

Met Asn Lys Leu Asn Glu Leu Glu Lys Ile Cys Glu Ile Leu Gln Ala
            1300                1305                1310

Glu Lys Tyr Glu Leu Val Thr Glu Leu Asn Asp Ser Arg Ser Glu Cys
            1315                1320                1325

Ile Thr Ala Thr Arg Lys Met Ala Glu Glu Val Gly Lys Leu Leu Asn
            1330                1335                1340

Glu Val Lys Ile Leu Asn Asp Asp Ser Gly Leu Leu His Gly Glu Leu
1345                1350                1355                1360

Val Glu Asp Ile Pro Gly Gly Glu Phe Gly Glu Gln Pro Asn Glu Gln
            1365                1370                1375

His Pro Val Ser Leu Ala Pro Leu Asp Glu Ser Asn Ser Tyr Glu His
            1380                1385                1390

Leu Thr Leu Ser Asp Lys Glu Val Gln Met His Phe Ala Glu Leu Gln
            1395                1400                1405

Glu Lys Phe Leu Ser Leu Gln Ser Glu His Lys Ile Leu His Asp Gln
            1410                1415                1420

His Cys Gln Met Ser Ser Lys Met Ser Glu Leu Gln Thr Tyr Val Asp
1425                1430                1435                1440

Ser Leu Lys Ala Glu Asn Leu Val Leu Ser Thr Asn Leu Arg Asn Phe
            1445                1450                1455

Gln Gly Asp Leu Val Lys Glu Met Gln Leu Gly Leu Glu Glu Gly Leu
            1460                1465                1470

Val Pro Ser Leu Ser Ser Ser Cys Val Pro Asp Ser Ser Leu Ser
            1475                1480                1485

Ser Leu Gly Asp Ser Ser Phe Tyr Arg Ala Leu Leu Glu Gln Thr Gly
            1490                1495                1500

Asp Met Ser Leu Leu Ser Asn Leu Glu Gly Ala Val Ser Ala Asn Gln
1505                1510                1515                1520

Cys Ser Val Asp Glu Val Phe Cys Ser Ser Leu Gln Thr Tyr Val Asp
            1525                1530                1535

Ser Leu Lys Ala Glu Asn Leu Val Leu Ser Thr Asn Leu Arg Asn Phe
            1540                1545                1550
```

```
Gln Gly Asp Leu Val Lys Glu Met Gln Leu Gly Leu Glu Gly Leu
        1555                1560                1565

Val Pro Ser Leu Ser Ser Ser Cys Val Pro Asp Ser Ser Ser Leu Ser
        1570                1575                1580

Ser Leu Gly Asp Ser Ser Phe Tyr Arg Ala Leu Leu Glu Gln Thr Gly
1585                1590                1595                1600

Asp Met Ser Leu Leu Ser Asn Leu Glu Gly Val Val Ser Ala Asn Gln
        1605                1610                1615

Cys Ser Val Asp Glu Val Phe Cys Ser Ser Leu Gln Glu Glu Asn Leu
        1620                1625                1630

Thr Arg Lys Glu Thr Pro Ser Ala Pro Ala Lys Gly Val Glu Glu Leu
        1635                1640                1645

Glu Ser Leu Cys Glu Val Tyr Arg Gln Ser Leu Glu Lys Leu Glu Glu
        1650                1655                1660

Lys Met Glu Ser Gln Gly Ile Met Lys Asn Lys Glu Ile Gln Glu Leu
1665                1670                1675                1680

Glu Gln Leu Leu Ser Ser Glu Arg Gln Glu Leu Asp Cys Leu Arg Lys
        1685                1690                1695

Gln Tyr Leu Ser Glu Asn Glu Gln Trp Gln Gln Lys Leu Thr Ser Val
        1700                1705                1710

Thr Leu Glu Met Glu Ser Lys Leu Ala Ala Glu Lys Lys Gln Thr Glu
        1715                1720                1725

Gln Leu Ser Leu Glu Leu Glu Val Ala Arg Leu Gln Leu Gln Gly Leu
        1730                1735                1740

Asp Leu Ser Ser Arg Ser Leu Leu Gly Ile Asp Thr Glu Asp Ala Ile
1745                1750                1755                1760

Gln Gly Arg Asn Glu Ser Cys Asp Ile Ser Lys Glu His Thr Ser Glu
        1765                1770                1775

Thr Thr Glu Arg Thr Pro Lys His Asp Val His Gln Ile Cys Asp Lys
        1780                1785                1790

Asp Ala Gln Gln Asp Leu Asn Leu Asp Ile Glu Lys Ile Thr Glu Thr
        1795                1800                1805

Gly Ala Val Lys Pro Thr Gly Glu Cys Ser Gly Glu Gln Ser Pro Asp
        1810                1815                1820

Thr Asn Tyr Glu Pro Pro Gly Glu Asp Lys Thr Gln Gly Ser Ser Glu
1825                1830                1835                1840

Cys Ile Ser Glu Leu Ser Phe Ser Gly Pro Asn Ala Leu Val Pro Met
        1845                1850                1855

Asp Phe Leu Gly Asn Gln Glu Asp Ile His Asn Leu Gln Leu Arg Val
        1860                1865                1870

Lys Glu Thr Ser Asn Glu Asn Leu Arg Leu Leu His Val Ile Glu Asp
        1875                1880                1885

Arg Asp Arg Lys Val Glu Ser Leu Leu Asn Glu Met Lys Glu Leu Asp
        1890                1895                1900

Ser Lys Leu His Leu Gln Glu Val Gln Leu Met Thr Lys Ile Glu Ala
1905                1910                1915                1920

Cys Ile Glu Leu Glu Lys Ile Val Gly Glu Leu Lys Lys Glu Asn Ser
        1925                1930                1935

Asp Leu Ser Glu Lys Leu Glu Tyr Phe Ser Cys Asp His Gln Glu Leu
        1940                1945                1950

Leu Gln Arg Val Glu Thr Ser Glu Gly Leu Asn Ser Asp Leu Glu Met
        1955                1960                1965

His Ala Asp Lys Ser Ser Arg Glu Asp Ile Gly Asp Asn Val Ala Lys
        1970                1975                1980
```

Val Asn Asp Ser Trp Lys Glu Arg Phe Leu Asp Val Glu Asn Glu Leu
1985                1990                1995                2000

Ser Arg Ile Arg Ser Glu Lys Ala Ser Ile Glu His Glu Ala Leu Tyr
            2005                2010                2015

Leu Glu Ala Asp Leu Glu Val Val Gln Thr Glu Lys Leu Cys Leu Glu
            2020                2025                2030

Lys Asp Asn Glu Asn Lys Gln Lys Val Ile Val Cys Leu Glu Glu
            2035                2040                2045

Leu Ser Val Val Thr Ser Glu Arg Asn Gln Leu Arg Gly Glu Leu Asp
            2050                2055                2060

Thr Met Ser Lys Lys Thr Thr Ala Leu Asp Gln Leu Ser Glu Lys Met
2065                2070                2075                2080

Lys Glu Lys Thr Gln Glu Leu Glu Ser His Gln Ser Glu Cys Leu His
            2085                2090                2095

Cys Ile Gln Val Ala Glu Ala Glu Val Lys Glu Lys Thr Glu Leu Leu
            2100                2105                2110

Gln Thr Leu Ser Ser Asp Val Ser Glu Leu Leu Lys Asp Lys Thr His
            2115                2120                2125

Leu Gln Glu Lys Leu Gln Ser Leu Glu Lys Asp Ser Gln Ala Leu Ser
            2130                2135                2140

Leu Thr Lys Cys Glu Leu Glu Asn Gln Ile Ala Gln Leu Asn Lys Glu
2145                2150                2155                2160

Lys Glu Leu Leu Val Lys Glu Ser Glu Ser Leu Gln Ala Arg Leu Ser
            2165                2170                2175

Glu Ser Asp Tyr Glu Lys Leu Asn Val Ser Lys Ala Leu Glu Ala Ala
            2180                2185                2190

Leu Val Glu Lys Gly Glu Phe Ala Leu Arg Leu Ser Ser Thr Gln Glu
            2195                2200                2205

Glu Val His Gln Leu Arg Arg Gly Ile Glu Lys Leu Arg Val Arg Ile
            2210                2215                2220

Glu Ala Asp Glu Lys Lys Gln Leu His Ile Ala Glu Lys Leu Lys Glu
2225                2230                2235                2240

Arg Glu Arg Glu Asn Asp Ser Leu Lys Asp Lys Val Glu Asn Leu Glu
            2245                2250                2255

Arg Glu Leu Gln Met Ser Glu Glu Asn Gln Glu Leu Val Ile Leu Asp
            2260                2265                2270

Ala Glu Asn Ser Lys Ala Glu Val Glu Thr Leu Lys Thr Gln Ile Glu
            2275                2280                2285

Glu Met Ala Arg Ser Leu Lys Ile Phe Glu Leu Asp Leu Val Thr Leu
            2290                2295                2300

Arg Ser Glu Lys Glu Asn Leu Thr Lys Gln Ile Gln Glu Lys Gln Gly
2305                2310                2315                2320

Gln Leu Ser Glu Leu Asp Lys Leu Leu Ser Ser Phe Lys Ser Leu Leu
            2325                2330                2335

Glu Glu Lys Glu Gln Ala Glu Ile Gln Ile Lys Glu Glu Ser Lys Thr
            2340                2345                2350

Ala Val Glu Met Leu Gln Asn Gln Leu Lys Glu Leu Asn Glu Ala Val
            2355                2360                2365

Ala Ala Leu Cys Gly Asp Gln Glu Ile Met Lys Ala Thr Gln Gln Ser
            2370                2375                2380

Leu Asp Pro Pro Ile Glu Glu Glu His Gln Leu Arg Asn Ser Ile Glu
2385                2390                2395                2400

```
Lys  Leu  Arg  Ala  Arg  Leu  Glu  Ala  Asp  Glu  Lys  Lys  Gln  Leu  Cys  Val
              2405                     2410                     2415

Leu  Gln  Gln  Leu  Lys  Glu  Ser  Glu  His  His  Ala  Asp  Leu  Leu  Lys  Gly
                   2420                     2425                     2430

Arg  Val  Glu  Asn  Leu  Glu  Arg  Glu  Leu  Glu  Ile  Ala  Arg  Thr  Asn  Gln
              2435                     2440                     2445

Glu  His  Ala  Ala  Leu  Glu  Ala  Glu  Asn  Ser  Lys  Gly  Glu  Val  Glu  Thr
              2450                     2455                     2460

Leu  Lys  Ala  Lys  Ile  Glu  Gly  Met  Thr  Gln  Ser  Leu  Arg  Gly  Leu  Glu
2465                     2470                     2475                     2480

Leu  Asp  Val  Val  Thr  Ile  Arg  Ser  Glu  Lys  Glu  Asn  Leu  Thr  Asn  Glu
                   2485                     2490                     2495

Leu  Gln  Lys  Glu  Gln  Glu  Arg  Ile  Ser  Glu  Leu  Glu  Ile  Ile  Asn  Ser
                   2500                     2505                     2510

Ser  Phe  Glu  Asn  Ile  Leu  Gln  Glu  Lys  Glu  Gln  Glu  Lys  Val  Gln  Met
                   2515                     2520                     2525

Lys  Glu  Lys  Ser  Ser  Thr  Ala  Met  Glu  Met  Leu  Gln  Thr  Gln  Leu  Lys
              2530                     2535                     2540

Glu  Leu  Asn  Glu  Arg  Val  Ala  Ala  Leu  His  Asn  Asp  Gln  Glu  Ala  Cys
2545                     2550                     2555                     2560

Lys  Ala  Lys  Glu  Gln  Asn  Leu  Ser  Ser  Gln  Val  Glu  Cys  Leu  Glu  Leu
                   2565                     2570                     2575

Glu  Lys  Ala  Gln  Leu  Leu  Gln  Gly  Leu  Asp  Glu  Ala  Lys  Asn  Asn  Tyr
              2580                     2585                     2590

Ile  Val  Leu  Gln  Ser  Ser  Val  Lys  Gly  Leu  Ile  Gln  Glu  Val  Glu  Asp
              2595                     2600                     2605

Gly  Lys  Gln  Lys  Leu  Glu  Lys  Lys  Asp  Glu  Glu  Ile  Ser  Arg  Leu  Lys
              2610                     2615                     2620

Asn  Gln  Ile  Gln  Asp  Gln  Glu  Gln  Leu  Val  Ser  Lys  Leu  Ser  Gln  Val
2625                     2630                     2635                     2640

Glu  Gly  Glu  His  Gln  Leu  Trp  Lys  Glu  Gln  Asn  Leu  Glu  Leu  Arg  Asn
                   2645                     2650                     2655

Leu  Thr  Val  Glu  Leu  Glu  Gln  Lys  Ile  Gln  Val  Leu  Gln  Ser  Lys  Asn
                   2660                     2665                     2670

Ala  Ser  Leu  Gln  Asp  Thr  Leu  Glu  Val  Leu  Gln  Ser  Ser  Tyr  Lys  Asn
              2675                     2680                     2685

Leu  Glu  Asn  Glu  Leu  Glu  Leu  Thr  Lys  Met  Asp  Lys  Met  Ser  Phe  Val
              2690                     2695                     2700

Glu  Lys  Val  Asn  Lys  Met  Thr  Ala  Lys  Glu  Thr  Glu  Leu  Gln  Arg  Glu
2705                     2710                     2715                     2720

Met  His  Glu  Met  Ala  Gln  Lys  Thr  Ala  Glu  Leu  Gln  Glu  Glu  Leu  Ser
                   2725                     2730                     2735

Gly  Glu  Lys  Asn  Arg  Leu  Ala  Gly  Glu  Leu  Gln  Leu  Leu  Leu  Glu  Glu
              2740                     2745                     2750

Ile  Lys  Ser  Ser  Lys  Asp  Gln  Leu  Lys  Glu  Leu  Thr  Leu  Glu  Asn  Ser
              2755                     2760                     2765

Glu  Leu  Lys  Lys  Ser  Leu  Asp  Cys  Met  His  Lys  Asp  Gln  Val  Glu  Lys
              2770                     2775                     2780

Glu  Gly  Lys  Val  Arg  Glu  Glu  Ile  Ala  Glu  Tyr  Gln  Leu  Arg  Leu  His
2785                     2790                     2795                     2800

Glu  Ala  Glu  Lys  Lys  His  Gln  Ala  Leu  Leu  Leu  Asp  Thr  Asn  Lys  Gln
                   2805                     2810                     2815

Tyr  Glu  Val  Glu  Ile  Gln  Thr  Tyr  Arg  Glu  Lys  Leu  Thr  Ser  Lys  Glu
              2820                     2825                     2830
```

```
Glu  Cys  Leu  Ser  Ser  Gln  Lys  Leu  Glu  Ile  Asp  Leu  Leu  Lys  Ser  Ser
          2835                2840                    2845

Lys  Glu  Glu  Leu  Asn  Asn  Ser  Leu  Lys  Ala  Thr  Thr  Gln  Ile  Leu  Glu
2850                     2855                    2860

Glu  Leu  Lys  Lys  Thr  Lys  Met  Asp  Asn  Leu  Lys  Tyr  Val  Asn  Gln  Leu
2865                2870                    2875                         2880

Lys  Lys  Glu  Asn  Glu  Arg  Ala  Gln  Gly  Lys  Met  Lys  Leu  Leu  Ile  Lys
               2885                    2890                         2895

Ser  Cys  Lys  Gln  Leu  Glu  Glu  Lys  Glu  Ile  Leu  Gln  Lys  Glu  Leu
          2900                    2905                    2910

Ser  Gln  Leu  Gln  Ala  Ala  Gln  Glu  Lys  Gln  Lys  Thr  Gly  Thr  Val  Met
          2915                    2920                    2925

Asp  Thr  Lys  Val  Asp  Glu  Leu  Thr  Thr  Glu  Ile  Lys  Glu  Leu  Lys  Glu
     2930                     2935                    2940

Thr  Leu  Glu  Glu  Lys  Thr  Lys  Glu  Ala  Asp  Glu  Tyr  Leu  Asp  Lys  Tyr
2945                2950                    2955                         2960

Cys  Ser  Leu  Leu  Ile  Ser  His  Glu  Lys  Leu  Glu  Lys  Ala  Lys  Glu  Met
                    2965                    2970                    2975

Leu  Glu  Thr  Gln  Val  Ala  His  Leu  Cys  Ser  Gln  Gln  Ser  Lys  Gln  Asp
               2980                    2985                    2990

Ser  Arg  Gly  Ser  Pro  Leu  Leu  Gly  Pro  Val  Val  Pro  Gly  Pro  Ser  Pro
               2995                    3000                    3005

Ile  Pro  Ser  Val  Thr  Glu  Lys  Arg  Leu  Ser  Ser  Gly  Gln  Asn  Lys  Ala
     3010                     3015                    3020

Ser  Gly  Lys  Arg  Gln  Arg  Ser  Ser  Gly  Ile  Trp  Glu  Asn  Gly  Arg  Gly
3025                3030                    3035                         3040

Pro  Thr  Pro  Ala  Thr  Pro  Glu  Ser  Phe  Ser  Lys  Lys  Ser  Lys  Lys  Ala
               3045                    3050                    3055

Val  Met  Ser  Gly  Ile  His  Pro  Ala  Glu  Asp  Thr  Glu  Gly  Thr  Glu  Phe
               3060                    3065                    3070

Glu  Pro  Glu  Gly  Leu  Pro  Glu  Val  Val  Lys  Lys  Gly  Phe  Ala  Asp  Ile
               3075                    3080                    3085

Pro  Thr  Gly  Lys  Thr  Ser  Pro  Tyr  Ile  Leu  Arg  Arg  Thr  Thr  Met  Ala
     3090                     3095                    3100

Thr  Arg  Thr  Ser  Pro  Arg  Leu  Ala  Ala  Gln  Lys  Leu  Ala  Leu  Ser  Pro
3105                     3110                    3115                    3120

Leu  Ser  Leu  Gly  Lys  Glu  Asn  Leu  Ala  Glu  Ser  Ser  Lys  Pro  Thr  Ala
               3125                    3130                    3135

Gly  Gly  Ser  Arg  Ser  Gln  Lys  Val  Lys  Val  Ala  Gln  Arg  Ser  Pro  Val
               3140                    3145                    3150

Asp  Ser  Gly  Thr  Ile  Leu  Arg  Glu  Pro  Thr  Thr  Lys  Ser  Val  Pro  Val
     3155                     3160                    3165

Asn  Asn  Leu  Pro  Glu  Arg  Ser  Pro  Thr  Asp  Ser  Pro  Arg  Glu  Gly  Leu
     3170                     3175                    3180

Arg  Val  Lys  Arg  Gly  Arg  Leu  Val  Pro  Ala  Pro  Lys  Leu  Asp  Trp  Ser
3185                     3190                    3195                    3200

Gln  Leu  Ala  Val  Arg  Thr  Val  Arg  Ser  Ser  Glu  Ala  Leu  Cys  Val  Ser
                    3205                    3210                         3215

Asp  Pro  Trp  Glu  Val  Gln  Ser  Leu  Ile  Asp  Arg  Leu  Cys  Leu  Gln  Asp
               3220                    3225                    3230

Phe  Ser  Leu  Val  Arg  Ala  Cys  Phe  Ile  Ser  Glu  Glu  Lys  Thr  Ile  Pro
               3235                    3240                    3245
```

( 2 ) INFORMATION FOR SEQ ID NO:2:

( i ) SEQUENCE CHARACTERISTICS:
        ( A ) LENGTH: 10136 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: HUMAN ( x i ) SEQUENCE DESCRIPTION: SEQ ID NO:2:

| | | | | | | |
|---|---|---|---|---|---|---|
| GGAGAAGCGG | GCGAATTGGG | CACCGGTGGC | GGCTGCGGGC | AGTTTGAATT | AGACTCTGGG | 60 |
| CTCCAGCCCG | CCGAAGCCGC | GCCAGAACTG | TACTCTCCGA | GAGGTCGTTT | TCCCGTCCCC | 120 |
| GAGAGCAAGT | TTATTTACAA | ATGTTGGAGT | AATAAAGAAG | GCAGAACAAA | ATGAGCTGGG | 180 |
| CTTTGGAAGA | ATGGAAAGAA | GGGCTGCCTA | CAAGAACTCT | TCAGAAAATT | CAAGAGCTTG | 240 |
| AAGGACAGCT | TGACAAACTG | AAGAAGGAAA | AGCAGCAAAG | GCAGTTTCAG | CTTGACAGTC | 300 |
| TCGAGGCTGC | GCCGCAGAAG | CAAACACAGA | AGGTTGAAAA | TGAAAAAACC | GAGGGTACAA | 360 |
| ACCTGAAAAG | GGAGAATCAA | AGATTGATGG | AAATATGTGA | AAGTCTGGAG | AAAACTAAGC | 420 |
| AGAAGATTTC | TCATGAACTT | CAAGTCAAGG | AGTCACAAGT | GAATTTCCAG | GAAGGACAAC | 480 |
| TGAATTCAGG | CAAAAAACAA | ATAGAAAAAC | TGGAACAGGA | ACTTAAAAGG | TGTAAATCTG | 540 |
| AGCTTGAAAG | AAGCCAACAA | GCTGCGCAGT | CTGCAGATGT | CTCTCTGAAT | CCATGCAATA | 600 |
| CACCACAAAA | AATTTTTACA | ACTCCACTAA | CACCAAGTCA | ATATTATAGT | GGTTCCAAGT | 660 |
| ATGAAGATCT | AAAAGAAAAA | TATAATAAAG | AGGTTGAAGA | ACGAAAAAGA | TTAGAGGCAG | 720 |
| AGGTTAAAGC | CTTGCAGGCT | AAAAAAGCAA | GCCAGACTCT | TCCACAAGCC | ACCATGAATC | 780 |
| ACCGCGACAT | TGCCCGGCAT | CAGGCTTCAT | CATCTGTGTT | CTCATGGCAG | CAAGAGAAGA | 840 |
| CCCCAAGTCA | TCTTTCATCT | AATTCTCAAA | GAACTCCAAT | TAGGAGAGAT | TTCTCTGCAT | 900 |
| CTTACTTTTC | TGGGGAACTA | GAGGTGACTC | CAAGTCGATC | AACTTTGCAA | ATAGGGAAAA | 960 |
| GAGATGCTAA | TAGCAGTTTC | TTTGGCAATT | CTAGCAGTCC | TCATCTTTTG | GATCAATTAA | 1020 |
| AAGCGCAGAA | TCAAGAGCTA | AGAAACAAGA | TTAATGAGTT | GGAACTACGC | CTGCAAGGAC | 1080 |
| ATGAAAAGA | AATGAAAGGC | CAAGTGAATA | AGTTTCAAGA | ACTCCAACTC | CAACTGGAGA | 1140 |
| AAGCAAAAGT | GGAATTAATT | GAAAAGAGA | AAGTTTTGAA | CAAATGTAGG | GATGAACTAG | 1200 |
| TGAGAACAAC | AGCACAATAC | GACCAGGCGT | CAACCAAGTA | TACTGCATTG | GAACAAAAAC | 1260 |
| TGAAAAAATT | GACGGAAGAT | TTGAGTTGTC | AGCGACAAAA | TGCAGAAAGT | GCCAGATGTT | 1320 |
| CTCTGGAACA | GAAAATTAAG | GAAAAGAAA | AGGAGTTTCA | GAGGAGCTC | TCCCGTCAAC | 1380 |
| AGCGTTCTTT | CCAAACACTG | GACCAGGAGT | GCATCCAGAT | GAAGGCCAGA | CTCACCCAGG | 1440 |
| AGTTACAGCA | AGCCAAGAAT | ATGCACAACG | TCCTGCAGGC | TGAACTGGAT | AAACTCACAT | 1500 |
| CAGTAAAGCA | ACAGCTAGAA | AACAATTTGG | AAGAGTTTAA | GCAAAAGTTG | TGCAGAGCTG | 1560 |
| AACAGGCGTT | CCAGGCGAGT | CAGATCAAGG | AGAATGAGCT | GAGGAGAAGC | ATGGAGGAAA | 1620 |
| TGAAGAAGGA | AAACAACCTC | CTTAAGAGTC | ACTCTGAGCA | AAAGGCCAGA | GAAGTCTGCC | 1680 |
| ACCTGGAGGC | AGAACTCAAG | AACATCAAAC | AGTGTTTAAA | TCAGAGCCAG | AATTTTGCAG | 1740 |
| AAGAAATGAA | AGCGAAGAAT | ACCTCTCAGG | AAACCATGTT | AAGAGATCTT | CAAGAAAAAA | 1800 |
| TAAATCAGCA | AGAAAACTCC | TTGACTTTAG | AAAAACTGAA | GCTTGCTGTG | GCTGATCTGG | 1860 |

| | | | | | | |
|---|---|---|---|---|---|---|
| AAAAGCAGCG | AGATTGTTCT | CAAGACCTTT | TGAAGAAAAG | AGAACATCAC | ATTGAACAAC | 1920 |
| TTAATGATAA | GTTAAGCAAG | ACAGAGAAAG | AGTCCAAAGC | CTTGCTGAGT | GCTTTAGAGT | 1980 |
| TAAAAAAGAA | AGAATATGAA | GAATTGAAAG | AAGAGAAAAC | TCTGTTTTCT | TGTTGGAAAA | 2040 |
| GTGAAAACGA | AAAACTTTTA | ACTCAGATGG | AATCAGAAAA | GGAAAACTTG | CAGAGTAAAA | 2100 |
| TTAATCACTT | GGAAACTTGT | CTGAAGACAC | AGCAAATAAA | AAGTCATGAA | TACAACGAGA | 2160 |
| GAGTAAGAAC | GCTGGAGATG | GACAGAGAAA | ACCTAAGTGT | CGAGATCAGA | AACCTTCACA | 2220 |
| ACGTGTTAGA | CAGTAAGTCA | GTGGAGGTAG | AGACCCAGAA | ACTAGCTTAT | ATGGAGCTAC | 2280 |
| AGCAGAAAGC | TGAGTTCTCA | GATCAGAAAC | ATCAGAAGGA | AATAGAAAAT | ATGTGTTTGA | 2340 |
| AGACTTCTCA | GCTTACTGGG | CAAGTTGAAG | ATCTAGAACA | CAAGCTTCAG | TTACTGTCAA | 2400 |
| ATGAAATAAT | GGACAAAGAC | CGGTGTTACC | AAGACTTGCA | TGCCGAATAT | GAGAGCCTCA | 2460 |
| GGGATCTGCT | AAAATCCAAA | GATGCTTCTC | TGGTGACAAA | TGAAGATCAT | CAGAGAAGTC | 2520 |
| TTTTGGCTTT | TGATCAGCAG | CCTGCCATGC | ATCATTCCTT | TGCAAATATA | ATTGGAGAAC | 2580 |
| AAGGAAGCAT | GCCTTCAGAG | AGGAGTGAAT | GTCGTTTAGA | AGCAGACCAA | AGTCCGAAAA | 2640 |
| ATTCTGCCAT | CCTACAAAAT | AGAGTTGATT | CACTTGAATT | TTCATTAGAG | TCTCAAAAAC | 2700 |
| AGATGAACTC | AGACCTGCAA | AAGCAGTGTG | AAGAGTTGGT | GCAAATCAAA | GGAGAAATAG | 2760 |
| AAGAAAATCT | CATGAAAGCA | GAACAGATGC | ATCAAAGTTT | TGTGGCTGAA | ACAAGTCAGC | 2820 |
| GCATTAGTAA | GTTACAGGAA | GACACTTCTG | CTCACCAGAA | TGTTGTTGCT | GAAACCTTAA | 2880 |
| GTGCCCTTGA | GAACAAGGAA | AAAGAGCTGC | AACTTTTAAA | TGATAAGGTA | GAAACTGAGC | 2940 |
| AGGCAGAGAT | TCAAGAATTA | AAAAGAGCA | ACCATCTACT | TGAAGACTCT | CTAAAGGAGC | 3000 |
| TACAACTTTT | ATCCGAAACC | CTAAGCTTGG | AGAAGAAAGA | AATGAGTTCC | ATCATTTCTT | 3060 |
| TAAATAAAAG | GGAAATTGAA | GAGCTGACCC | AAGAGAATGG | GACTCTTAAG | GAAATTAATG | 3120 |
| CATCCTTAAA | TCAAGAGAAG | ATGAACTTAA | TCCAGAAAAG | TGAGAGTTTT | GCAAACTATA | 3180 |
| TAGATGAAAG | GGAGAAAAGC | ATTTCAGAGT | TATCTGATCA | GTACAAGCAA | GAAAAACTTA | 3240 |
| TTTTACTACA | AAGATGTGAA | GAAACCGGAA | ATGCATATGA | GGATCTTAGT | CAAAAATACA | 3300 |
| AAGCAGCACA | GGAAAAGAAT | TCTAAATTAG | AATGCTTGCT | AAATGAATGC | ACTAGTCTTT | 3360 |
| GTGAAAATAG | GAAAAATGAG | TTGGAACAGC | TAAAGGAAGC | ATTTGCAAAG | GAACACCAAG | 3420 |
| AATTCTTAAC | AAAATTAGCA | TTTGCTGAAG | AAAGAAATCA | GAATCTGATG | CTAGAGTTGG | 3480 |
| AGACAGTGCA | GCAAGCTCTG | AGATCTGAGA | TGACAGATAA | CCAAAACAAT | TCTAAGAGCG | 3540 |
| AGGCTGGTGG | TTTAAAGCAA | GAAATCATGA | CTTTAAAGGA | AGAACAAAAC | AAAATGCAAA | 3600 |
| AGGAAGTTAA | TGACTTATTA | CAAGAGAATG | AACAGCTGAT | GAAGGTAATG | AAGACTAAAC | 3660 |
| ATGAATGTCA | AAATCTAGAA | TCAGAACCAA | TTAGGAACTC | TGTGAAAGAA | AGAGAGAGTG | 3720 |
| AGAGAAATCA | ATGTAATTTT | AAACCTCAGA | TGGATCTTGA | AGTTAAAGAA | ATTTCTCTAG | 3780 |
| ATAGTTATAA | TGCGCAGTTG | GTGCAATTAG | AAGCTATGCT | AAGAAATAAG | GAATTAAAAC | 3840 |
| TTCAGGAAAG | TGAGAAGGAG | AAGGAGTGCC | TGCAGCATGA | ATTACAGACA | ATTAGAGGAG | 3900 |
| ATCTTGAAAC | CAGCAATTTG | CAAGACATGC | AGTCACAAGA | AATTAGTGGC | CTTAAAGACT | 3960 |
| GTGAAATAGA | TGCGGAAGAA | AAGTATATTT | CAGGGCCTCA | TGAGTTGTCA | ACAAGTCAAA | 4020 |
| ACGACAATGC | ACACCTTCAG | TGCTCTCTGC | AAACAACAAT | GAACAAGCTG | AATGAGCTAG | 4080 |
| AGAAAATATG | TGAAATACTG | CAGGCTGAAA | AGTATGAACT | CGTAACTGAG | CTGAATGATT | 4140 |
| CAAGGTCAGA | ATGTATCACA | GCAACTAGGA | AAATGGCAGA | AGAGGTAGGG | AAACTACTAA | 4200 |
| ATGAAGTTAA | AATATTAAAT | GATGACAGTG | GTCTTCTCCA | TGGTGAGTTA | GTGGAAGACA | 4260 |

| | | | | | |
|---|---|---|---|---|---|
| TACCAGGAGG | TGAATTTGGT | GAACAACCAA | ATGAACAGCA | CCCTGTGTCT | TTGGCTCCAT | 4320
| TGGACGAGAG | TAATTCCTAC | GAGCACTTGA | CATTGTCAGA | CAAAGAAGTT | CAAATGCACT | 4380
| TTGCCGAATT | GCAAGAGAAA | TTCTTATCTT | TACAAAGTGA | ACACAAAATT | TTACATGATC | 4440
| AGCACTGTCA | GATGAGCTCT | AAAATGTCAG | AGCTGCAGAC | CTATGTTGAC | TCATTAAAGG | 4500
| CCGAAAATTT | GGTCTTGTCA | ACGAATCTGA | GAAACTTTCA | AGGTGACTTG | GTGAAGGAGA | 4560
| TGCAGCTGGG | CTTGGAGGAG | GGGCTCGTTC | CATCCCTGTC | ATCCTCTTGT | GTGCCTGACA | 4620
| GCTCTAGTCT | TAGCAGTTTG | GGAGACTCCT | CCTTTTACAG | AGCTCTTTTA | GAACAGACAG | 4680
| GAGATATGTC | TCTTTTGAGT | AATTTAGAAG | GGGCTGTTTC | AGCAAACCAG | TGCAGTGTAG | 4740
| ATGAAGTATT | TTGCAGCAGT | CTGCAGACCT | ATGTTGACTC | ATTAAAGGCC | GAAAATTTGG | 4800
| TCTTGTCAAC | GAATCTGAGA | AACTTTCAAG | GTGACTTGGT | GAAGGAGATG | CAGCTGGGCT | 4860
| TGGAGGAGGG | GCTCGTTCCA | TCCCTGTCAT | CCTCTTGTGT | GCCTGACAGC | TCTAGTCTTA | 4920
| GCAGTTTGGG | AGACTCCTCC | TTTTACAGAG | CTCTTTTAGA | ACAGACAGGA | GATATGTCTC | 4980
| TTTTGAGTAA | TTTAGAAGGG | GTTGTTTCAG | CAAACCAGTG | CAGTGTAGAT | GAAGTATTTT | 5040
| GCAGCAGTCT | GCAGGAGGAG | AATCTGACCA | GGAAAGAAAC | CCCTTCGGCC | CCAGCGAAGG | 5100
| GTGTTGAAGA | GCTTGAGTCC | CTCTGTGAGG | TGTACCGGCA | GTCCCTCGAG | AAGCTAGAAG | 5160
| AGAAAATGGA | AAGTCAAGGG | ATTATGAAAA | ATAAGGAAAT | TCAAGAGCTC | GAGCAGTTAT | 5220
| TAAGTTCTGA | AAGGCAAGAG | CTTGACTGCC | TTAGGAAGCA | GTATTTGTCA | GAAAATGAAC | 5280
| AGTGGCAACA | GAAGCTGACA | AGCGTGACTC | TGGAGATGGA | GTCCAAGTTG | GCGGCAGAAA | 5340
| AGAAACAGAC | GGAACAACTG | TCACTTGAGC | TGGAAGTAGC | ACGACTCCAG | CTACAAGGTC | 5400
| TGGACTTAAG | TTCTCGGTCT | TTGCTTGGCA | TCGACACAGA | AGATGCTATT | CAAGGCCGAA | 5460
| ATGAGAGCTG | TGACATATCA | AAAGAACATA | CTTCAGAAAC | TACAGAAAGA | ACACCAAAGC | 5520
| ATGATGTTCA | TCAGATTTGT | GATAAAGATG | CTCAGCAGGA | CCTCAATCTA | GACATTGAGA | 5580
| AAATAACTGA | GACTGGTGCA | GTGAAACCCA | CAGGAGAGTG | CTCTGGGGAA | CAGTCCCCAG | 5640
| ATACCAATTA | TGAGCCTCCA | GGGGAAGATA | AAACCCAGGG | CTCTTCAGAA | TGCATTTCTG | 5700
| AATTGTCATT | TTCTGGTCCT | AATGCTTTGG | TACCTATGGA | TTTCCTGGGG | AATCAGGAAG | 5760
| ATATCCATAA | TCTTCAACTG | CGGGTAAAAG | AGACATCAAA | TGAGAATTTG | AGATTACTTC | 5820
| ATGTGATAGA | GGACCGTGAC | AGAAAAGTTG | AAAGTTTGCT | AAATGAAATG | AAAGAATTAG | 5880
| ACTCAAAACT | CCATTTACAG | GAGGTACAAC | TAATGACCAA | AATTGAAGCA | TGCATAGAAT | 5940
| TGGAAAAAAT | AGTTGGGGAA | CTTAAGAAAG | AAAACTCAGA | TTTAAGTGAA | AAATTGGAAT | 6000
| ATTTTTCTTG | TGATCACCAG | GAGTTACTCC | AGAGAGTAGA | AACTTCTGAA | GGCCTCAATT | 6060
| CTGATTTAGA | AATGCATGCA | GATAAATCAT | CACGTGAAGA | TATTGGAGAT | AATGTGGCCA | 6120
| AGGTGAATGA | CAGCTGGAAG | GAGAGATTTC | TTGATGTGGA | AAATGAGCTG | AGTAGGATCA | 6180
| GATCGGAGAA | AGCTAGCATT | GAGCATGAAG | CCCTCTACCT | GGAGGCTGAC | TTAGAGGTAG | 6240
| TTCAAACAGA | GAAGCTATGT | TTAGAAAAAG | ACAATGAAAA | TAAGCAGAAG | GTTATTGTCT | 6300
| GCCTTGAAGA | AGAACTCTCA | GTGGTCACAA | GTGAGAGAAA | CCAGCTTCGT | GGAGAATTAG | 6360
| ATACTATGTC | AAAAAAAACC | ACGGCACTGG | ATCAGTTGTC | TGAAAAAATG | AAGGAGAAAA | 6420
| CACAAGAGCT | TGAGTCTCAT | CAAAGTGAGT | GTCTCCATTG | CATTCAGGTG | GCAGAGGCAG | 6480
| AGGTGAAGGA | AAAGACGGAA | CTCCTTCAGA | CTTTGTCCTC | TGATGTGAGT | GAGCTGTTAA | 6540
| AAGACAAAAC | TCATCTCCAG | GAAAAGCTGC | AGAGTTTGGA | AAAGGACTCA | CAGGCACTGT | 6600
| CTTTGACAAA | ATGTGAGCTG | GAAAACCAAA | TTGCACAACT | GAATAAAGAG | AAAGAATTGC | 6660

```
TTGTCAAGGA  ATCTGAAAGC  CTGCAGGCCA  GACTGAGTGA  ATCAGATTAT  GAAAAGCTGA    6720
ATGTCTCCAA  GGCCTTGGAG  GCCGCACTGG  TGGAGAAAGG  TGAGTTCGCA  TTGAGGCTGA    6780
GCTCAACACA  GGAGGAAGTG  CATCAGCTGA  GAAGAGGCAT  CGAGAAACTG  AGAGTTCGCA    6840
TTGAGGCCGA  TGAAAAGAAG  CAGCTGCACA  TCGCAGAGAA  ACTGAAAGAA  CGCGAGCGGG    6900
AGAATGATTC  ACTTAAGGAT  AAAGTTGAGA  ACCTTGAAAG  GGAATTGCAG  ATGTCAGAAG    6960
AAAACCAGGA  GCTAGTGATT  CTTGATGCCG  AGAATTCCAA  AGCAGAAGTA  GAGACTCTAA    7020
AAACACAAAT  AGAAGAGATG  GCCAGAAGCC  TGAAGATTTT  TGAATTAGAC  CTTGTCACGT    7080
TAAGGTCTGA  AAAAGAAAAT  CTGACAAAAC  AAATACAAGA  AAAACAAGGT  CAGTTGTCAG    7140
AACTAGACAA  GTTACTCTCT  TCATTTAAAA  GTCTGTTAGA  AGAAAAGGAG  CAAGCAGAGA    7200
TACAGATCAA  AGAAGAATCT  AAAACTGCAG  TGGAGATGCT  TCAGAATCAG  TTAAAGGAGC    7260
TAAATGAGGC  AGTAGCAGCC  TTGTGTGGTG  ACCAAGAAAT  TATGAAGGCC  ACAGAACAGA    7320
GTCTAGACCC  ACCAATAGAG  GAAGAGCATC  AGCTGAGAAA  TAGCATTGAA  AAGCTGAGAG    7380
CCCGCCTAGA  AGCTGATGAA  AAGAAGCAGC  TCTGTGTCTT  ACAACAACTG  AAGGAAAGTG    7440
AGCATCATGC  AGATTTACTT  AAGGGTAGAG  TGGAGAACCT  TGAAAGAGAG  CTAGAGATAG    7500
CCAGGACAAA  CCAAGAGCAT  GCAGCTCTTG  AGGCAGAGAA  TTCCAAGGA   GAGGTAGAGA    7560
CCCTAAAAGC  AAAAATAGAA  GGGATGACCC  AAAGTCTGAG  AGGTCTGGAA  TTAGATGTTG    7620
TTACTATAAG  GTCAGAAAAA  GAAAATCTGA  CAAATGAATT  ACAAAAAGAG  CAAGAGCGAA    7680
TATCTGAATT  AGAAATAATA  AATTCATCAT  TTGAAAATAT  TTTGCAAGAA  AAAGAGCAAG    7740
AGAAAGTACA  GATGAAAGAA  AAATCAAGCA  CTGCCATGGA  GATGCTTCAA  ACACAATTAA    7800
AAGAGCTCAA  TGAGAGAGTG  GCAGCCCTGC  ATAATGACCA  AGAAGCCTGT  AAGGCCAAAG    7860
AGCAGAATCT  TAGTAGTCAA  GTAGAGTGTC  TTGAACTTGA  GAAGGCTCAG  TTGCTACAAG    7920
GCCTTGATGA  GGCCAAAAAT  AATTATATTG  TTTTGCAATC  TTCAGTGAAA  GGCCTCATTC    7980
AAGAAGTAGA  AGATGGCAAG  CAGAAACTGG  AGAAGAAGGA  TGAAGAAATC  AGTAGACTGA    8040
AAAATCAAAT  TCAAGACCAA  GAGCAGCTTG  TCTCTAAACT  GTCCCAGGTG  GAAGGAGAGC    8100
ACCAACTTTG  GAAGGAGCAA  AACTTAGAAC  TGAGAAATCT  GACGGTGGAA  TTGGAGCAGA    8160
AGATCCAAGT  GCTACAATCC  AAAAATGCCT  CTTTGCAGGA  CACATTAGAA  GTGCTGCAGA    8220
GTTCTTACAA  GAATCTAGAG  AATGAGCTTG  AATTGACAAA  AATGGACAAA  ATGTCCTTTG    8280
TTGAAAAAGT  AAACAAAATG  ACTGCAAAGG  AAACTGAGCT  GCAGAGGGAA  ATGCATGAGA    8340
TGGCACAGAA  AACAGCAGAG  CTGCAAGAAG  AACTCAGTGG  AGAGAAAAAT  AGGCTAGCTG    8400
GAGAGTTGCA  GTTACTGTTG  GAAGAAATAA  AGAGCAGCAA  AGATCAATTG  AAGGAGCTCA    8460
CACTAGAAAA  TAGTGAATTG  AAGAAGAGCC  TAGATTGCAT  GCACAAAGAC  CAGGTGGAAA    8520
AGGAAGGGAA  AGTGAGAGAG  GAAATAGCTG  AATATCAGCT  ACGGCTTCAT  GAAGCTGAAA    8580
AGAAACACCA  GGCTTTGCTT  TTGGACACAA  ACAAACAGTA  TGAAGTAGAA  ATCCAGACAT    8640
ACCGAGAGAA  ATTGACTTCT  AAAGAAGAAT  GTCTCAGTTC  ACAGAAGCTG  AGATAGACC    8700
TTTTAAAGTC  TAGTAAAGAA  GAGCTCAATA  ATTCATTGAA  AGCTACTACT  CAGATTTTGG    8760
AAGAATTGAA  GAAAACCAAG  ATGGACAATC  TAAAATATGT  AAATCAGTTG  AAGAAGGAAA    8820
ATGAACGTGC  CCAGGGGAAA  ATGAAGTTGT  TGATCAAATC  CTGTAAACAG  CTGGAAGAGG    8880
AAAAGGAGAT  ACTGCAGAAA  GAACTCTCTC  AACTTCAAGC  TGCACAGGAG  AAGCAGAAAA    8940
CAGGTACTGT  TATGGATACC  AAGGTCGATG  AATTAACAAC  TGAGATCAAA  GAACTGAAAG    9000
AAACTCTTGA  AGAAAAAACC  AAGGAGGCAG  ATGAATACTT  GGATAAGTAC  TGTTCCTTGC    9060
```

| | | | | | |
|---|---|---|---|---|---|
| TTATAAGCCA | TGAAAAGTTA | GAGAAAGCTA | AAGAGATGTT | AGAGACACAA | GTGGCCCATC | 9120
| TGTGTTCACA | GCAATCTAAA | CAAGATTCCC | GAGGGTCTCC | TTTGCTAGGT | CCAGTTGTTC | 9180
| CAGGACCATC | TCCAATCCCT | TCTGTTACTG | AAAAGAGGTT | ATCATCTGGC | AAAATAAAG | 9240
| CTTCAGGCAA | GAGGCAAAGA | TCCAGTGGAA | TATGGGAGAA | TGGTAGAGGA | CCAACACCTG | 9300
| CTACCCCAGA | GAGCTTTTCT | AAAAAAAGCA | AGAAAGCAGT | CATGAGTGGT | ATTCACCCTG | 9360
| CAGAAGACAC | GGAAGGTACT | GAGTTTGAGC | CAGAGGGACT | TCCAGAAGTT | GTAAAGAAAG | 9420
| GGTTTGCTGA | CATCCCGACA | GGAAAGACTA | GCCCATATAT | CCTGCGAAGA | ACAACCATGG | 9480
| CAACTCGGAC | CAGCCCCCGC | CTGGCTGCAC | AGAAGTTAGC | GCTATCCCCA | CTGAGTCTCG | 9540
| GCAAAGAAAA | TCTTGCAGAG | TCCTCCAAAC | CAACAGCTGG | TGGCAGCAGA | TCACAAAAGG | 9600
| TCAAAGTTGC | TCAGCGGAGC | CCAGTAGATT | CAGGCACCAT | CCTCCAGAA  | CCCACCACGA | 9660
| AATCCGTCCC | AGTCAATAAT | CTTCCTGAGA | GAAGTCCGAC | TGACAGCCCC | AGAGAGGGCC | 9720
| TGAGGGTCAA | GCGAGGCCGA | CTTGTCCCAG | CCCCAAAGCT | GGACTGGAGT | CAACTGGCAG | 9780
| TGAGAACTGT | AAGGTCCAGC | GAAGCACTTT | GTGTGTCAGA | CCCTTGGGAG | GTGCAGTCAT | 9840
| TGATAGATAG | GCTGTGCCTA | CAGGACTTCT | CTTTAGTCAG | GGCATGCTTT | ATTAGTGAGG | 9900
| AGAAAACAAT | TCCTTAGAAG | TCTTAAATAT | ATTGTACTCT | TTAGATCTCC | CATGTGTAGG | 9960
| TATTGAAAAA | GTTGGAAGC  | ACTGATCACC | TGTTAGCATT | GCCATTCCTC | TACTGCAATG | 10020
| TAAATAGTAT | AAAGCTATGT | ATATAAAGCT | TTTTGGTAAT | ATGTTACAAT | TAAAATGACA | 10080
| AGCACTATAT | AAAAAAAAA  | AAAAAAAAA  | AAAAAAAAA  | AAAAAAAAA  | AAAAA      | 10136

(2) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CTTTTGCTTT CTCCAGTTGG      20

(2) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

TTGACGCCTG GTCGTATTG      19